(12) United States Patent
Karathanasis et al.

(10) Patent No.: US 11,065,202 B2
(45) Date of Patent: *Jul. 20, 2021

(54) MULTI-COMPONENT NANOCHAINS

(71) Applicant: CASE WESTERN RESERVE UNIVERSITY, Cleveland, OH (US)

(72) Inventors: Efstathios Karathanasis, Solon, OH (US); Watuthantrige Pubudu M Peiris, Cleveland, OH (US); Mark Griswold, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/209,866

(22) Filed: Dec. 4, 2018

(65) Prior Publication Data

US 2019/0307687 A1    Oct. 10, 2019

Related U.S. Application Data

(63) Continuation of application No. 15/262,863, filed on Sep. 12, 2016, now Pat. No. 10,143,653, which is a
(Continued)

(51) Int. Cl.
*A61K 9/127* (2006.01)
*A61P 35/00* (2006.01)
(Continued)

(52) U.S. Cl.
CPC ............ *A61K 9/127* (2013.01); *A61K 9/0019* (2013.01); *A61K 31/704* (2013.01); *A61K 38/16* (2013.01);
(Continued)

(58) Field of Classification Search
None
See application file for complete search history.

(56) References Cited

U.S. PATENT DOCUMENTS 9,439,966 B2 *  9/2016  Karathanasis ......... A61K 38/16
10,143,653 B2 * 12/2018  Karathanasis ..... A61K 41/0057
(Continued)

FOREIGN PATENT DOCUMENTS

WO         2005/055982 A2    6/2005
WO     WO-2013056092 A1 *   4/2013  ......... A61K 49/0438

OTHER PUBLICATIONS

PM Peiris, E Schmidt, M Calabrese, E Karathanasis. "Assembly of Linear Nano-Chains from Iron Oxide Nanospheres with Asymmetric Surface Chemistry." PLoS One, Jan. 2011, vol. 6 Issue 1, e15927, pp. 1-9. (Year: 2011).
(Continued)

*Primary Examiner* — Isaac Shomer
(74) *Attorney, Agent, or Firm* — Tarolli, Sundheim, Covell & Tummino LLP

(57) ABSTRACT

A multi-component nanochain for use in diagnostic and therapeutic applications includes at least three nanoparticles linked together to form the nanochain. At least one nanoparticle of the nanochain has an asymmetric surface chemistry defined by asymmetrically disposed first linkers and second linkers. The nanoparticles are linked to form the nanochain by linking first linkers and/or second linkers disposed on separate nanoparticles.

18 Claims, 18 Drawing Sheets

Specification includes a Sequence Listing.

Related U.S. Application Data continuation of application No. 14/351,420, filed as application No. PCT/US2012/060021 on Oct. 12, 2012, now Pat. No. 9,439,966.

(60) Provisional application No. 61/703,003, filed on Sep. 19, 2012, provisional application No. 61/546,350, filed on Oct. 12, 2011.

(51) Int. Cl.

| | | |
|---|---|---|
| *A61K 47/02* | (2006.01) | |
| *A61K 9/00* | (2006.01) | |
| *A61K 41/00* | (2020.01) | |
| *A61K 47/69* | (2017.01) | |
| *A61K 49/00* | (2006.01) | |
| *A61K 49/04* | (2006.01) | |
| *A61K 49/18* | (2006.01) | |
| *A61K 41/10* | (2020.01) | |
| *A61K 38/16* | (2006.01) | |
| *A61K 31/704* | (2006.01) | |
| *A61K 49/14* | (2006.01) | |

(52) U.S. Cl.
CPC .......... *A61K 41/0057* (2013.01); *A61K 41/10* (2020.01); *A61K 47/02* (2013.01); *A61K 47/6941* (2017.08); *A61K 49/0084* (2013.01); *A61K 49/0093* (2013.01); *A61K 49/0438* (2013.01); *A61K 49/0466* (2013.01); *A61K 49/14* (2013.01); *A61K 49/1824* (2013.01); *A61P 35/00* (2018.01); *Y10S 977/773* (2013.01); *Y10S 977/906* (2013.01); *Y10S 977/907* (2013.01); *Y10S 977/927* (2013.01); *Y10T 428/2982* (2015.01)

(56) References Cited

U.S. PATENT DOCUMENTS

| | | | |
|---|---|---|---|
| 10,729,652 B2 * | 8/2020 | Karathanasis | ....... A61K 33/242 |
| 2002/0010351 A1 | 1/2002 | Serhan | |
| 2002/0103517 A1 | 8/2002 | West et al. | |
| 2003/0044805 A1 | 3/2003 | Mirkin et al. | |
| 2004/0077844 A1 * | 4/2004 | Jacobson | ................ B05D 1/00 530/391.5 |
| 2005/0273143 A1 | 12/2005 | Kanzius et al. | |
| 2006/0083781 A1 | 4/2006 | Shastri et al. | |
| 2006/0233712 A1 | 10/2006 | Penades et al. | |
| 2009/0181101 A1 | 7/2009 | Rademacher et al. | |
| 2009/0221764 A1 | 9/2009 | Shumaker-Parry et al. | |

OTHER PUBLICATIONS

PM Peiris et al. "Imaging Metastasis Using an Integrin-Targeting Chain-Shaped Nanoparticle." ACS Nano, vol. 6 No. 10, published online Sep. 24, 2012, pp. 8783-8795. (Year: 2012).

PM Peiris et al. "Enhanced Delivery of Chemotherapy to Tumors Using a Multicomponent Nanochain with Radio-Frequency-Tunable Drug Release." ACS Nano, vol. 6 No. 5, published online Apr. 9, 2012, pp. 4157-4168. (Year: 2012).

PM Peiris et al. "Treatment of Invasive Brain Tumors Using a Chain-like Nanoparticle." Cancer Research, vol. 75(7), Apr. 1, 2015, pp. 1356-1365. (Year: 2015).

Chen, A Bose, GD Bothun. "Controlled Release from Bilayer-Decorated Magnetoliposomes via Electromagnetic Heating." v ACS Nano, vol. 4 No. 6, 2010, pp. 3215-3221, published on line May 27, 2010.

D Hanczyc, B Akerman, B Norden. "Short Oligonucleotides Aligned in Stretched Humid Matrix: Secondary DNA Structure invPoly(vinyl alcohol) Environment." Langmuir, vol. 28, 2012, pp. 6662-6669, Published Mar. 27, 2012.

H Moran, SM Wainerdi, TK Cherukuri, C Killrel, BJ Wiley, NW Nicholas, SA Curley, JS Kanzius, P Cherukuri. "Size-Dependent Joule Heating of Gold Nanoparticles Using Capacitively Coupled Radiofrequency Fields." Nano Research, vol. 2, 2009, pp. 400-405.

PM Peiris, A Abramowski, J Mcginnity, E Doolittle, R Toy, R Gopalakrishnan, S Shah, L Bauer, KB Ghaghada, C Hoimes, SM Brady-Kalnay, JP Basilion, MA Griswold, E Karathanasis. "Treatment of Invasive Brain Tumors Using a Chain-like Nanoparticle." Cancer Research, vol. 75(7), 2015, pp. OF1-0F10.

* cited by examiner

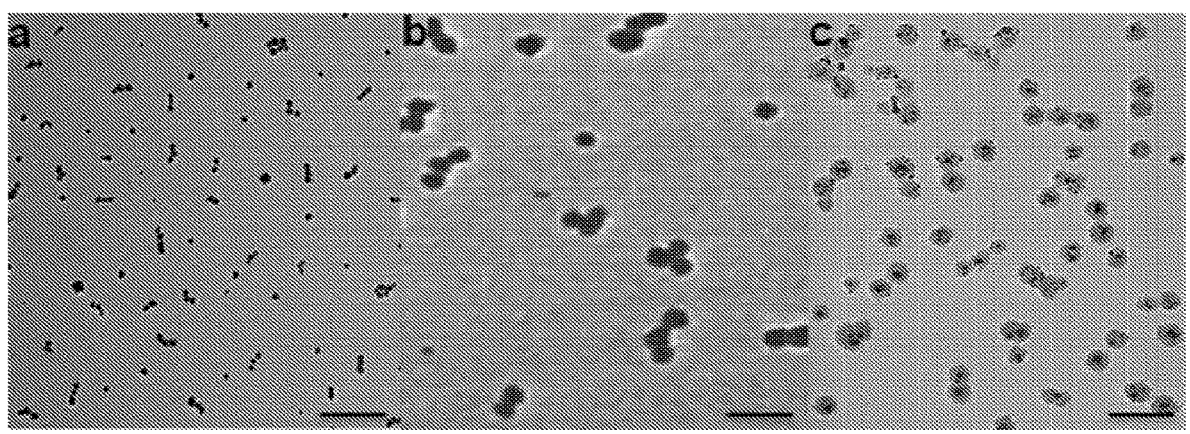
Figs. 8A-C

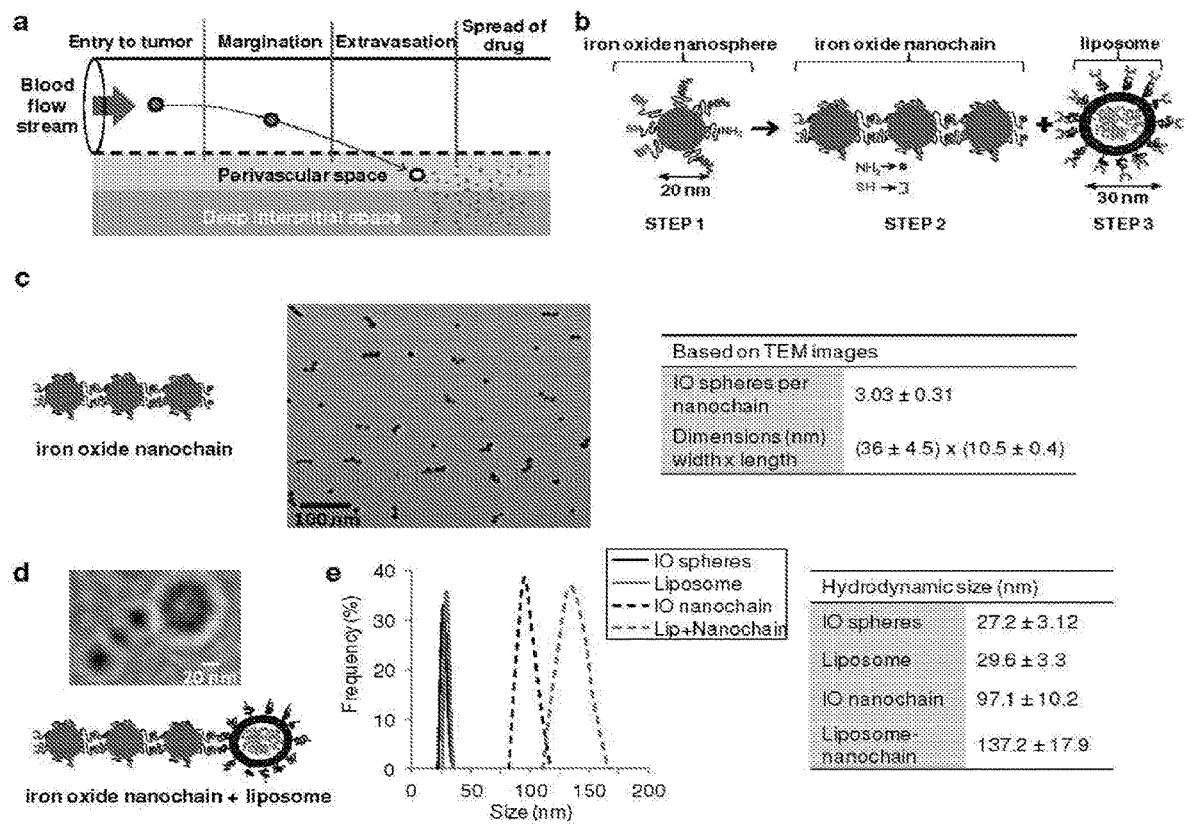
Figs. 9A-E

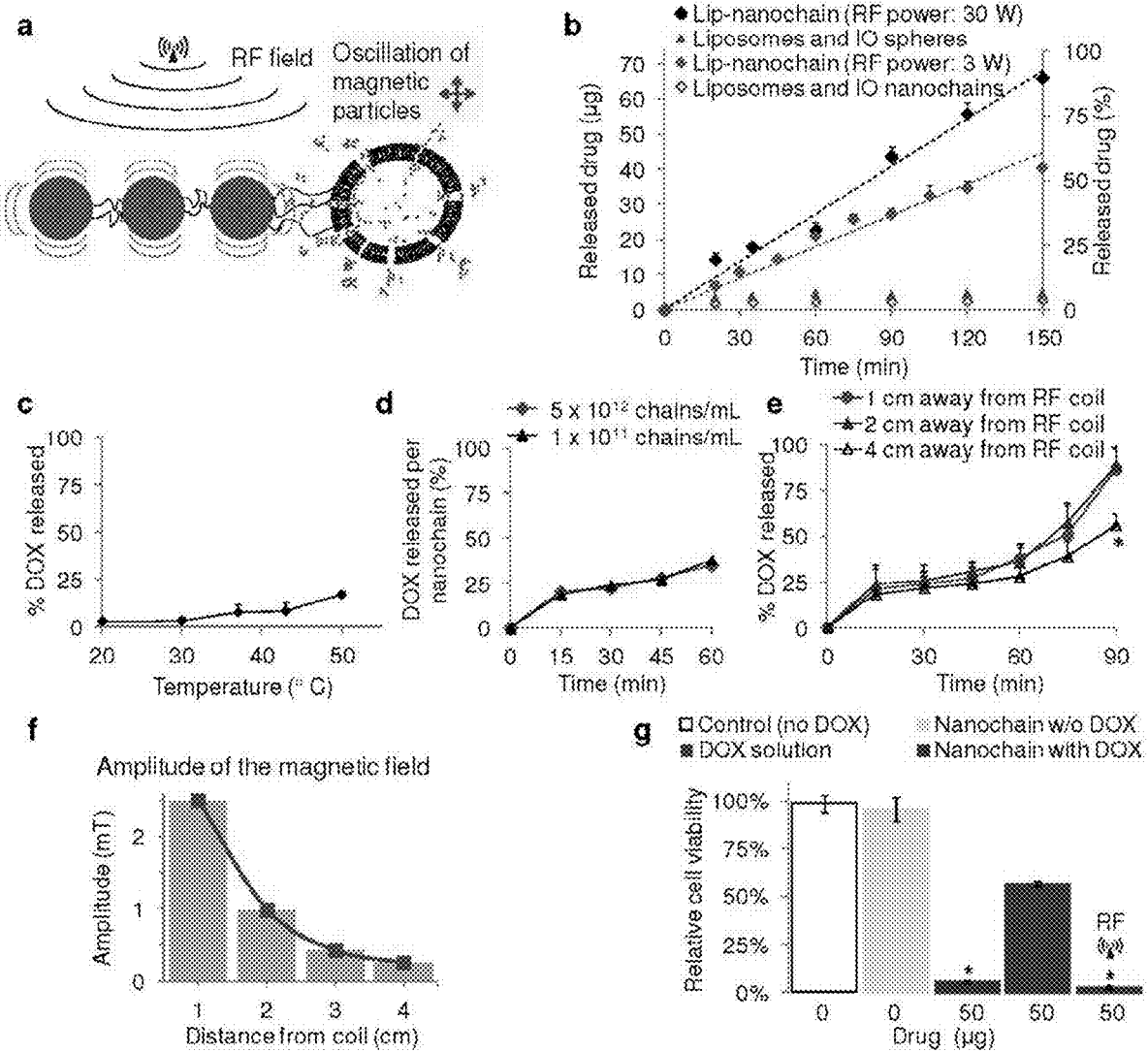
Figs. 10A-G

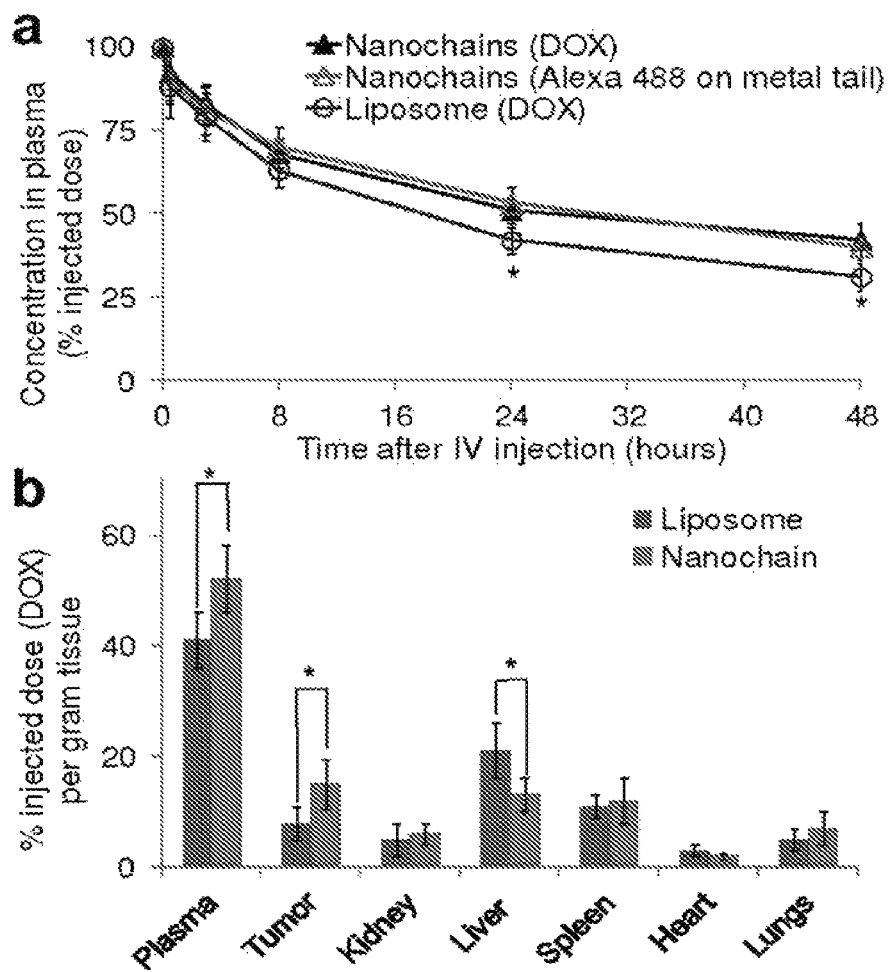
Figs. 11A-B

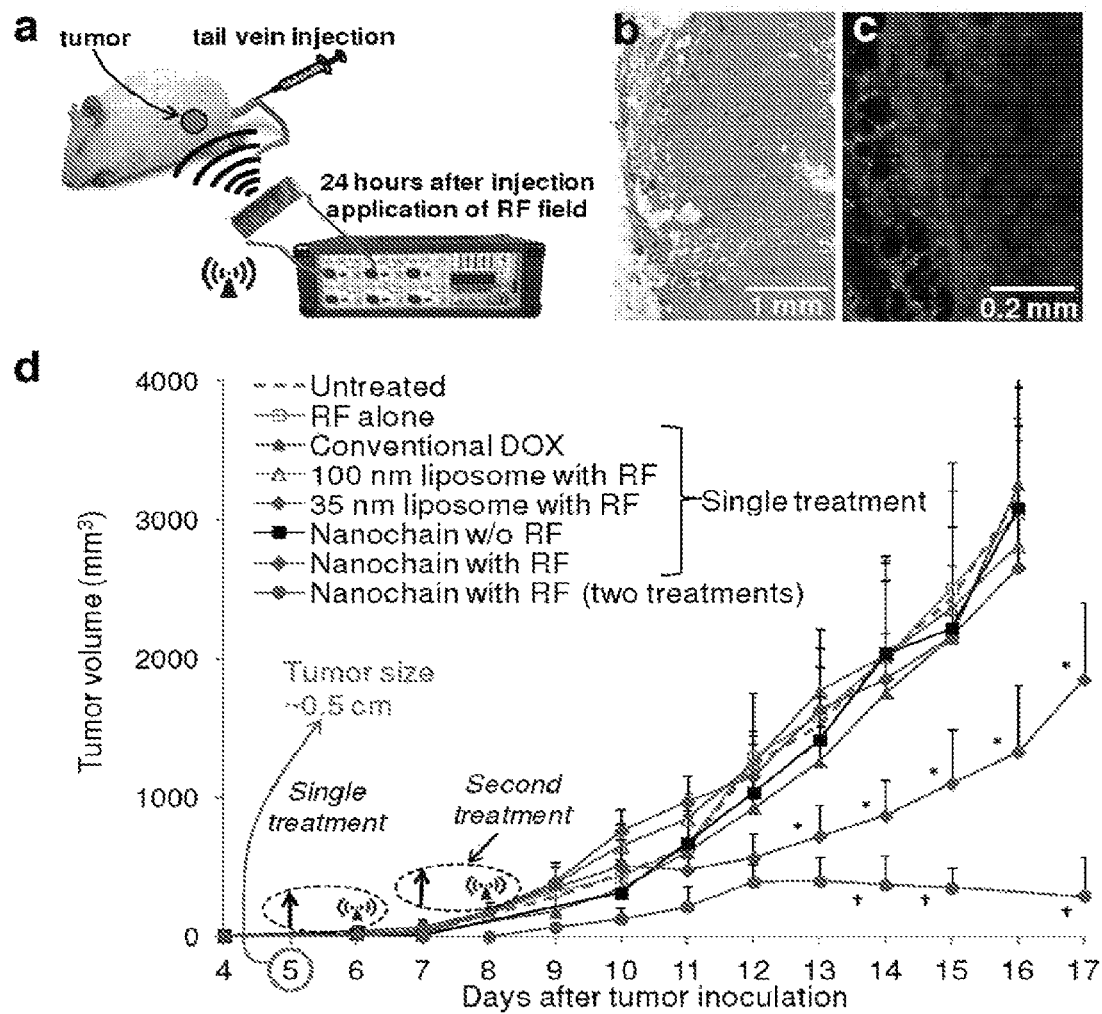
Figs. 12A-D

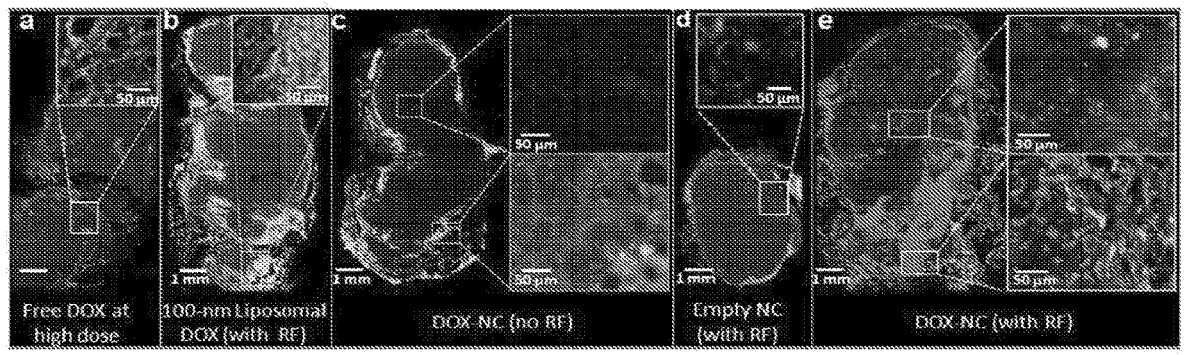
Figs. 13A-E
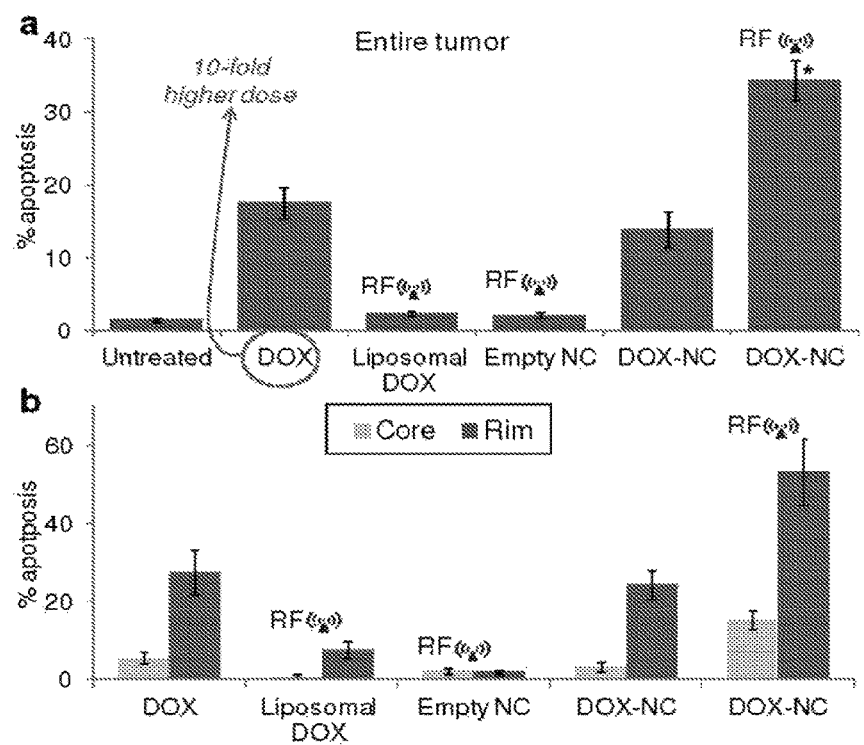
Figs. 14A-B

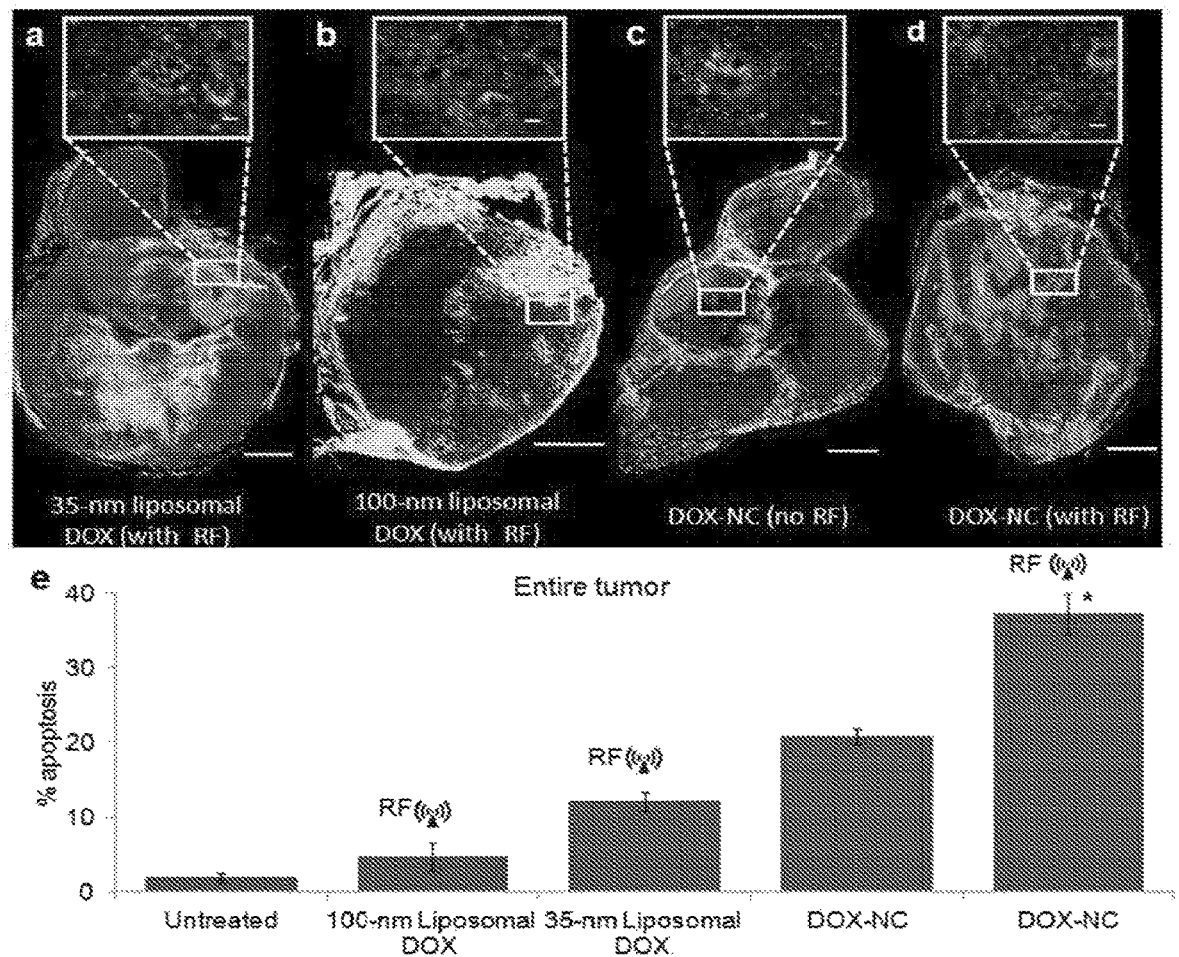
Figs. 15A-E

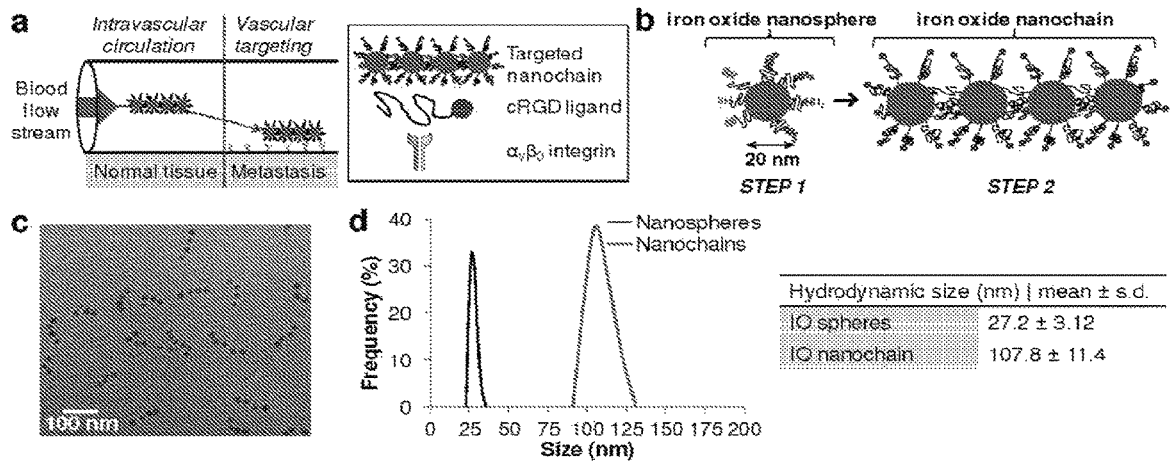
Figs. 16A-D
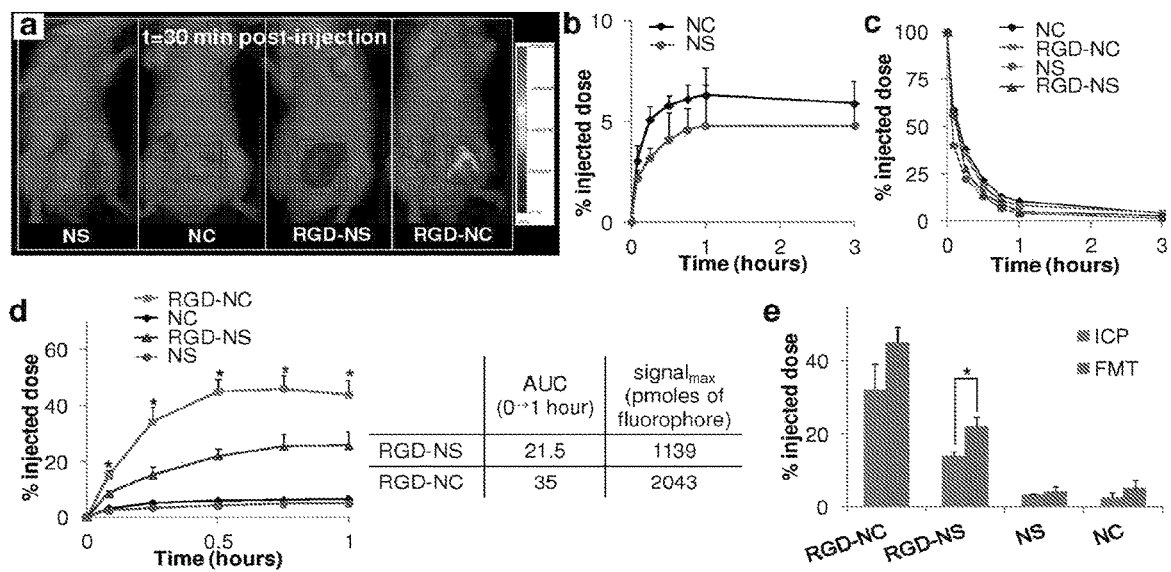
Figs. 17A-E

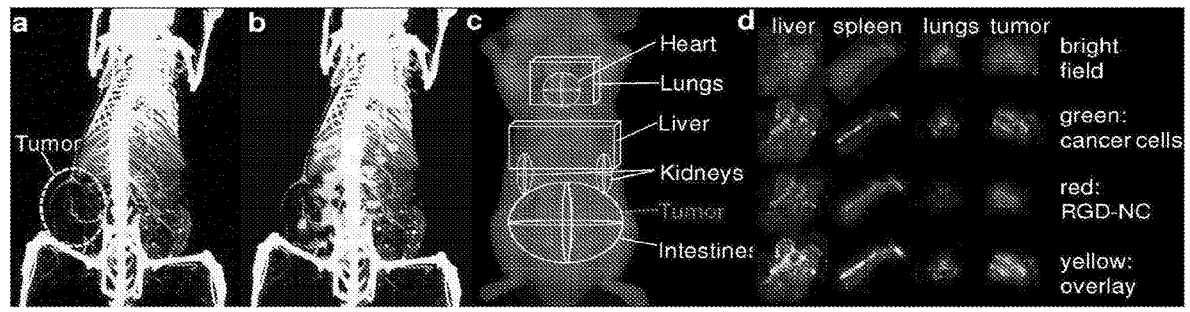
Figs. 18A-D
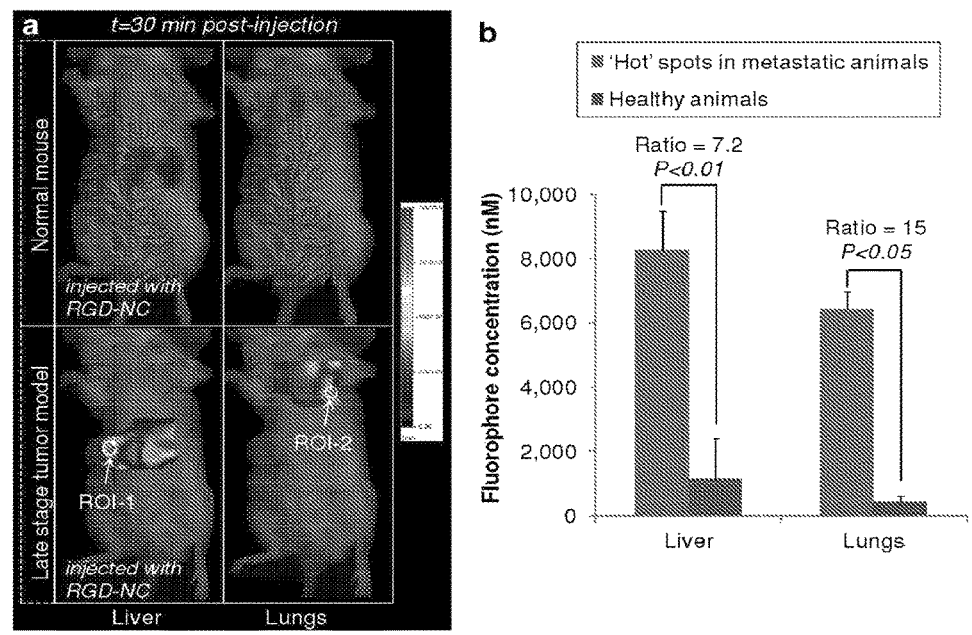
Figs. 19A-B

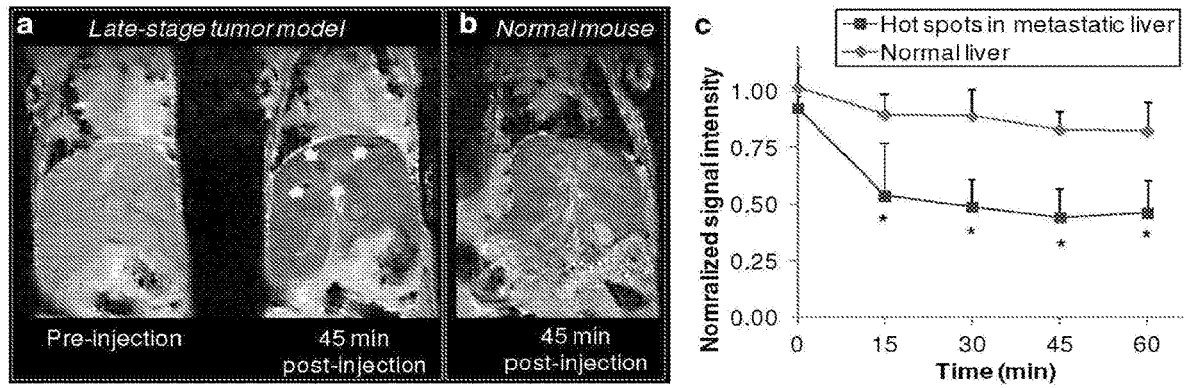
Figs. 20A-C
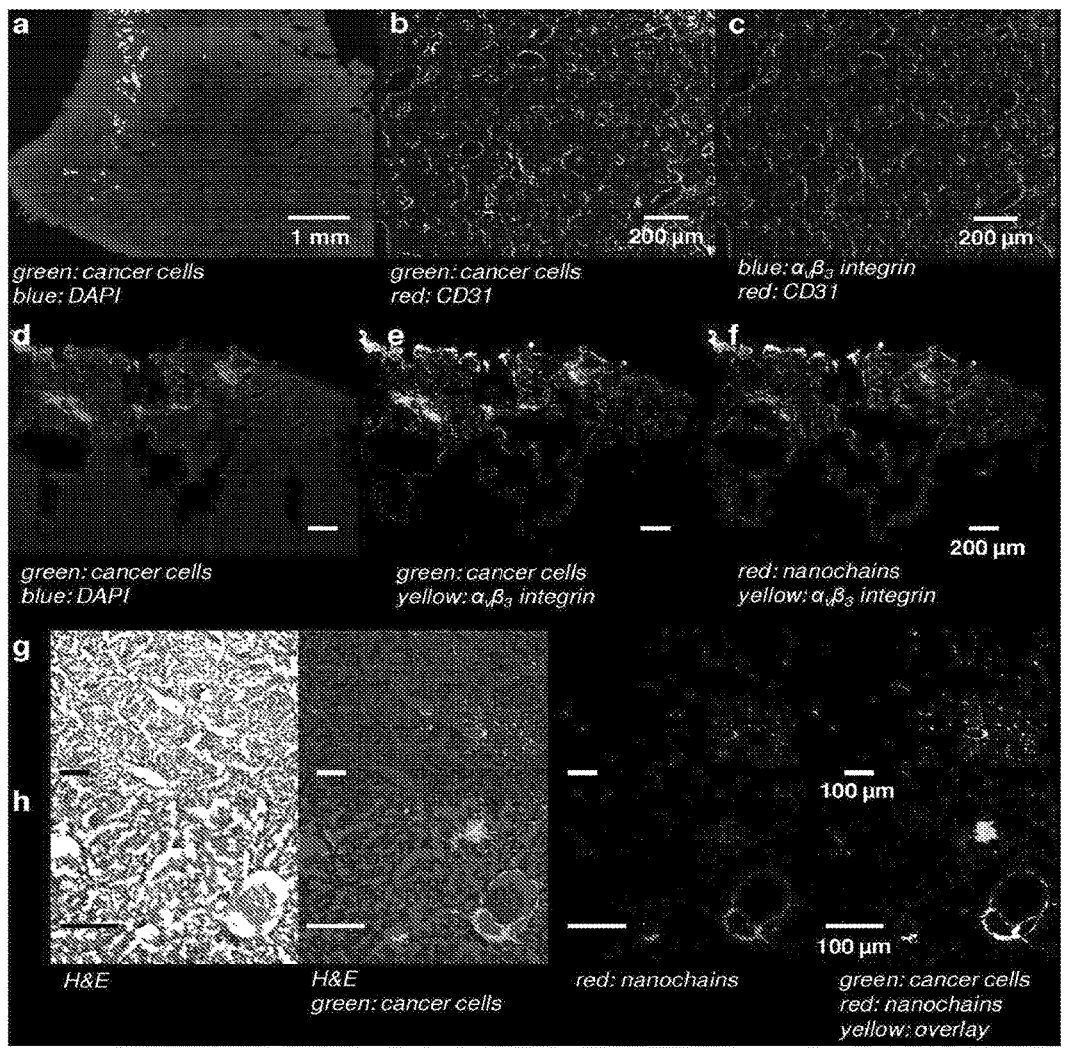
Figs. 21A-H

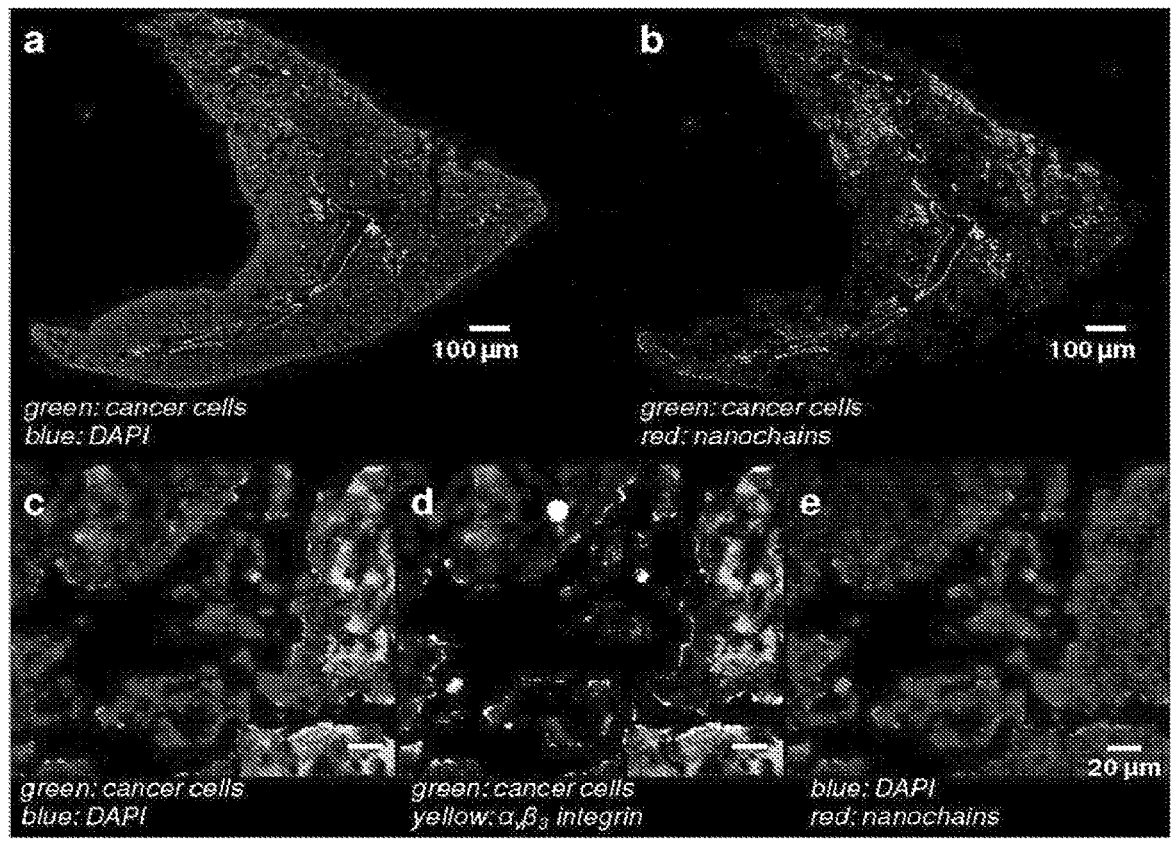
Figs. 22A-E

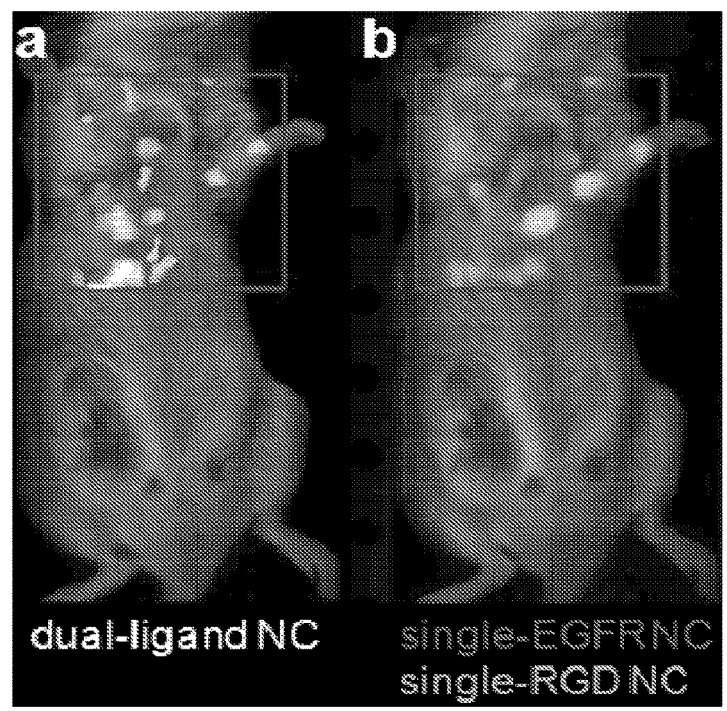
Figs. 23A-B
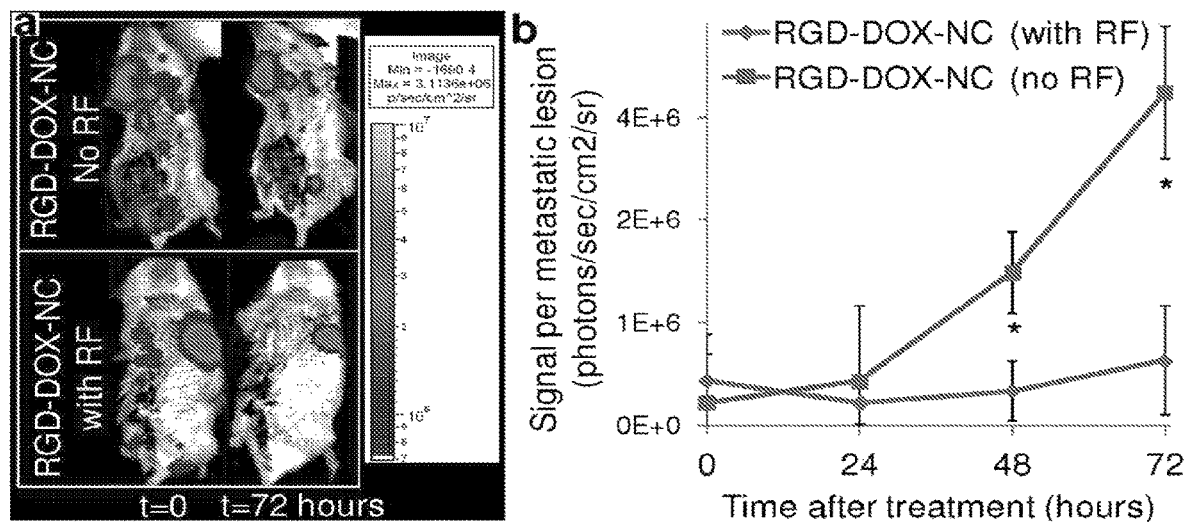
Figs. 24A-B

MULTI-COMPONENT NANOCHAINS

RELATED APPLICATION

This application is a continuation of U.S. application Ser. No. 15/262,863 filed Sep. 12, 2016, (now U.S. Pat. No. 10,143,653) which is a continuation of U.S. application Ser. No. 14/351,420, (now U.S. Pat. No. 9,439,966) filed Apr. 11, 2014, which is a National Stage Entry of PCT/US2012/060021, which claims priority from U.S. Provisional Application Ser. No. 61/703,003, filed Sep. 19, 2012 and U.S. Provisional Application Ser. No. 61/546,350, filed Oct. 12, 2011, the subject matter of which is incorporated herein by reference in their entirety.

TECHNICAL FIELD

This application relates to multi-component nanochains and to the use of multi-components nanochains for diagnostic and therapeutic applications.

BACKGROUND

Nanoparticles can be used as delivery vehicles for therapeutic and imaging agents with improved biodistribution and increased delivery efficiency to solid tumors. In particular, nanomedicine's greatest advantage over conventional therapies is its ability to combine more than one function by enabling the design of multifunctional nanoparticles that target, image, and destroy tumors. This has led to the development of various nanoparticle delivery systems such as liposomes, dendrimers, other lipidic and polymeric nanoparticles, and metal nanoparticles (e.g., iron oxide and gold). While the shape of the majority of these particles is spherical due to the methods of preparation, recent advances have fabricated oblate- and rod-shaped nanostructures suitable for biomedical applications, such as gold nanorods, nanoworms, and nanonecklaces. For example, the so-called nanoworms consist of iron oxide cores aligned along strands of high-molecular weight dextran. A nanonecklace was formed by attaching monofunctionalized gold nanoparticles onto polylysine.

SUMMARY

Embodiments described herein relate to a multi-component nanochain (i.e., nanochain) for use in diagnostic and therapeutic applications. The nanochain can include at least three nanoparticles linked together to form the nanochain. At least one nanoparticle of the nanochain has an asymmetric surface chemistry defined by asymmetrically disposed first linkers and second linkers. The nanoparticles can be linked to form the nanochain by linking first linkers and/or second linkers disposed on separate nanoparticles.

In some embodiments, the nanoparticles can have an average or nominal diameter of about 1 nm to about 50 nm and the nanochain can have a length less than about 200 nm and a width about 50 nm or less. The nanoparticles forming the nanochain can be the same or different and be selected from the group consisting of a metal nanoparticle, lipidic nanoparticle, polymer nanoparticle, liposome, or dendrimer.

In other embodiments, at least one nanoparticle can include or be linked to an imaging agent, therapeutic agent, and/or targeting moiety. The therapeutic agent can include, for example, an anti-cancer agent or anti-proliferative agent. The nanochain can also include multiple targeting moieties. The targeting moieties can be linked to surfaces of the nanoparticles and the spacing between the nanoparticles can be controlled to facilitate targeting of the nanoparticles to cells of a subject. The spacing and location of the targeting moieties on each nanoparticle can be controlled to facilitate delivery, targeting, and/or therapeutic efficacy of the nanochain when administered to a subject.

In some embodiments the nanochain can include at least two metal nanoparticles. At least one of the metal nanoparticles can be linked to a liposome, lipidic nanoparticle, or polymer nanoparticle that includes an imaging agent or therapeutic agent. The metal nanoparticles of the nanochain when administered to a subject can be responsive to energy, from a remote source that is effective to release the imaging agent or therapeutic agent from the liposome, lipidic nanoparticle, or polymer nanoparticle. In one example, the energy can be radiofrequency (RF) energy that causes mechanical oscillation or resonance of the metal nanoparticles that is effective to release the therapeutic agent or imaging agent from the liposome, lipidic nanoparticle, or polymer nanoparticle. The RF energy effective to release the therapeutic agent or imaging agent can be an amount less than that required to induce a substantial or significant localized temperature increase in the subject.

Other embodiments described herein relate to a method of forming a multi-component nanochain. The method includes defining an asymmetric surface chemistry on a plurality of nanoparticles so that each nanoparticle includes a first face with a first linker and second face with a second linker. The first linker and the second linker can be capable of binding to link separate nanoparticles. The nanoparticles are then assembled into nanochains using solid phase synthesis in which at least some of the nanoparticles are serially added to least other of the nanoparticles conjugated to a solid support.

Still other embodiments described herein relate to a system for delivering a therapeutic agent to cells or tissue of a subject. The system includes a multi-component nanochain that comprises at least three nanoparticles linked together to form the nanochain. At least one nanoparticle of the nanochain can have an asymmetric surface chemistry defined by asymmetrically disposed first linkers and second linkers. The nanoparticles can be linked to form the nanochain by linking first linkers and/or second linkers disposed on separate nanoparticles. At least one nanoparticle can include or being linked to a therapeutic agent.

In some embodiments, the multi-component nanochain of the system can include at least two metal nanoparticles and a liposome, lipidic nanoparticle, or polymer nanoparticle linked to one metal nanoparticle of the nanochain. The liposome, lipidic nanoparticle, or polymer nanoparticle can include, contain, and/or encapsulate the therapeutic agent. The metal nanoparticles can be responsive to energy, from a remote source that is effective to release the therapeutic agent from the liposome, lipidic nanoparticle, or polymer nanoparticle after administering the nanochain to a subject. The system can further include a remote energy source for supplying energy to the metal nanoparticles effective to release the therapeutic agent from the liposome, lipidic nanoparticle, or polymer nanoparticle. The remote energy source can be external the subject being treated.

In one example, the remote energy source can include a radiofrequency (RF) energy source that produces RF energy effective cause resonating or oscillating of the nanoparticles. The RF energy effective to release the therapeutic agent can be an amount less than that required to induce a substantial or significant localized temperature increase in the subject.

Other embodiments relate to a method of treating cancer in a subject. The method can include administering to the subject a multi-component nanochain that includes at least three nanoparticles linked together to form the nanochain. At least one nanoparticle of the nanochain can have an asymmetric surface chemistry defined by asymmetrically disposed first linkers and second linkers. The nanoparticles can be linked to form the nanochain by linking first linkers and/or second linkers disposed on separate nanoparticles. At least one nanoparticle can include or being linked to an anti-cancer agent or anti-proliferative agent.

Other embodiments described herein relate to a method or system of imaging a region of interest in a subject. The method or system can include administering to a subject a plurality of multi-component nanochains that include at least one contrast agent or imaging agent. The multi-component nanochain can include at least three nanoparticles linked to together to form the nanochain. At least one nanoparticle of the nanochain having asymmetric surface chemistry defined by asymmetrically disposed first linkers and second linkers. The nanoparticles can be linked to form the nanochain by linking first linkers and/or second linkers disposed on separate nanoparticles. The distribution of the nanochains in the subject can be detected in the region of interest using an imaging modality for detecting the contrast agent or imaging agent when the nanochain is administered to the subject.

BRIEF DESCRIPTION OF THE DRAWINGS

FIGS. 8(a-c) illustrate TEM images of linear nanochains assembled from (a) three 10 nm iron oxide nanospheres (NC-3×10), (b) three 30 nm iron oxide nanospheres (NC-3×30), and (c) two 30 nm iron oxide nanospheres sprinkled with 10 nm iron oxide nanospheres (NC-2×30(10)). Scale bar is 100 nm.

FIGS. 9(a-e) illustrate: (a) Schematic illustration of the required steps for the successful delivery of nanoparticle-based drug to tumors. (b) Diagram of the DOX-NC nanoparticle and its constituent components including a nanochain composed of three iron oxide (IO) spheres and one liposome. (c) TEM image of magnetic nanochains composed of three IO spheres. The table summarizes the main characteristics of the magnetic nanochains obtained from visual analysis of TEM images (minimum count was 200 particles; data presented as mean±s.d). (d) TEM image of a nanochain particle composed of three IO spheres and one DOX-loaded liposome. (e) Size distribution of the parent nanoparticles and DOX-loaded nanochains obtained by DLS measurements (data presented as mean±s.d.)

FIGS. 10(a-g) illustrate: (a) Schematic illustration of the defects on the liposome caused by 'vibration' of the IO spheres under an RF field. (b) Plot showing triggered release from DOX-NC particles using an RF field at 10 kHz and different energy outputs (the sample was located 1 cm away from the RF coil). The samples were exposed to the RF field for the entire duration of the experiment. Besides DOX-NC particles, the RF field (30 W) was applied to mixtures of liposomes with IO nanospheres or IO nanochains at a ratio of 1:3 (liposome: IO spheres). (c) Plot showing effect of temperature on the drug release from DOX-NC particles (incubation time was 60 min). (d) Plot showing drug release from DOX-NC particles at different particle concentration under an RF field at 10 kHz/30 W (the sample was located 1 cm away from the RF coil). (e) Plot showing drug release from DOX-NC particles at different distance from the RF source (RF field: 10 kHz/30 W). (f) Graph showing Amplitude of the magnetic field at different distances from the RF source (RF field: 10 kHz/30 W). (g) Graph showing cytotoxicity of DOX-NC (with or without RF) on 13762 MAT B III cells. Control treatments included black nanochains, free DOX, and liposomal DOX. The two data points marked with asterisks are statistically different compared to the other conditions (P<0.01).

FIGS. 11(a-b) illustrate: (a) Plot showing plasma clearance of DOX-loaded liposomes (100 nm in diameter) and DOX-NC in rats at a dose of 0.5 mg/kg DOX (n=5). Besides DOX, fluorescence spectroscopy was used to measure Alexa 488 on the iron oxide particles (*P<0.05). (b) Graph showing organ and tumor distribution 24 h after administration of the DOX-loaded liposomes and DOX-NC at a dose of 0.5 mg DOX/kg in the rat 13762 MAT B III tumor model (n=6; *P<0.05).

FIGS. 12(a-d) illustrate: (a) Schematic illustration of the therapeutic protocol. (b) Image of histological evaluation of the distribution of systemically administered DOX-NC particles (blue: Prussian blue stain) in a tumor. (c) Image of application of an RF field released DOX molecules (red) that localized in the nuclei of cancer cells (blue: DAPI). (d) Plot showing measurement of the tumor growth of 13763 MAT B III tumors in rats after systemic administration of DOX-NC at a dose of 0.5 mg/kg DOX (arrow; day 5) followed by application of the RF field (day 6). Control treatments included saline (untreated), RF alone, free DOX, 100-nm liposomal DOX (with RF), 35-nm liposomal DOX (with RF) and DOX-NC (without RF). Another group of animals received a second injection of DOX-NC (arrow; days 7) followed by RF application (day 8). Data points marked with asterisks are statistically significant relative to all the other single-treated groups. Data points marked with crosses are statistically significant relative to all groups (n=6; * and †P<0.05).

FIGS. 13(a-e) illustrate: (a) Fluorescence image of a histological section of a tumor 48 h after IV injection of free DOX at 5 mg/kg. The specific endothelial antigen CD31 was stained (green). Nuclei (blue) were stained with DAPI. Apoptotic cell nuclei were stained with TUNEL (red). (b) Fluorescence image showing no significant apoptosis was observed in a tumor 48 h after systemic administration of 100-nm liposomal DOX at 0.5 mg/kg (RF was applied 24 h after injection). (c) Fluorescence image showing few apoptotic cells were found in a tumor 48 h after systemic administration of DOX-NC at 0.5 mg/kg. (d) Fluorescence image showing negligible apoptosis was found in a tumor 48 h after systemic administration of an empty nanochain (RF was applied 24 h after injection). (e) Fluorescence image showing significant number of apoptotic cells were found in a tumor 48 h after systemic administration of liposomal DOX at 0.5 mg/kg (RF was applied 24 h after injection).

FIGS. 14(a-b) illustrate: (a) Graph showing A quantitative analysis of the fluorescence images was performed by comparing the total number of cancer and apoptotic cells of an entire tumor as measured in at least 20 histological sections per tumor (about 10,000 cells per section). The apoptotic effect on tumors treated with DOX-NC followed by RF was compared to the other DOX-based treatments (n=3 rats per group; * P<0.01). (b) Graph showing regional apoptosis in the tumor was measured based on the degree of vascularization. Using the endothelial cells staining (CD31), the well-vascularized rim of the tumor was distinguished from its core.

FIGS. 15(a-e) illustrate: (a) Fluorescence image showing a histological section of a tumor 48 h after IV injection of 35-nm liposomal DOX at 0.5 mg/kg (CD31: green, DAPI: blue, TUNEL: red). RF was applied 24 h after injection. The scale bar is 1 mm (scale bar of the inset is 50 µm) (b) Fluorescence image showing no significant apoptosis was observed in a tumor 48 h after systemic administration of 100-nm liposomal DOX at 0.5 mg/kg (RF was applied 24 h after injection). (c) Fluorescence image showing more apoptotic cells were found in a tumor 48 h after systemic administration of DOX-NC at 0.5 mg/kg. (d) Fluorescence image showing a significant number of apoptotic cells were found in a tumor 48 h after systemic administration of DOX-NC at 0.5 mg/kg followed by RF application 24 h after injection. (e) Graph showing a quantitative analysis of apoptosis was performed by comparing the total number of cancer and apoptotic cells of an entire tumor (minimum 20 histological sections per tumor; n=3 mice per group; * P<0.01).

FIGS. 16(a-d) illustrate: (a) Schematic illustration of the models for the successful delivery of RGD-NC nanoparticles to metastasis via vascular targeting. (b) Diagram of the RGD-NC nanoparticle and its constituent components. (c) TEM image of RGD-NC nanoparticles predominantly composed of four IO spheres. (d) Plots showing size distribution of the parent IO nanospheres and RGD-NC nanoparticles obtained by DLS measurements.

FIGS. 17(a-e) illustrate: (a) FMT images showing the accumulation of RGD-targeted and non-targeted IO spheres and nanochains in primary tumors at 30 min post-injection (dose: equal number of particles per kg of body weight). The nanoparticles of each formulation exhibited the same fluorescence signal per particle. (b) Plots showing quantification of the time-course of accumulation of the non-targeted nanospheres and nanochains in the tumor due to the EPR effect. (c) Plots showing time-course of the amount of nanoparticles in the heart as a measure of the blood residence time of each formulation. (d) Plots showing comparison of the intratumoral accumulation of targeted nanochains and nanospheres and their non-targeted variants in the first 1 hour after administration. It should be noted the range of x- and y-axis are different between FIGS. 15b and c. While the RGD-targeted IO spheres exhibited higher tumor accumulation than the non-targeted formulations, they were substantially outperformed by the RGD-NC nanoparticles (data presented as mean±standard deviation). (e) Graph showing the primary tumors of animals injected with NS, NC, RGD-NS or RGD-NC were perfused, excised, and weighted 30 min after administration. After digestion of the tissues, the iron concentration was measured using inductively coupled plasma optical emission spectroscopy (ICP-OES). Control animals were used to correct for background levels of endogenous iron. In the FMT and ICP measurements, data points marked with asterisks are statistically significant relative to all groups (n=6 animals per formulation; * P<0.05).

FIGS. 18(a-d) illustrate: (a) Micromorphological images of normal and tumor vasculature at 99 µm resolution of a metastatic 4T1 tumor (week 5) using a Siemens Inveon micro-CT and a liposome-based iodinated contrast agent. (b) Images showing co-registration of the micro-CT image with the FMT image of the same animal injected with the RGD-NC nanoparticles. (c) Images showing the location of the tumor and different organs as obtained from previously published work. (d) Ex vivo images of organs indicating the colocalization of RGD-NC particles and 4T1 metastatic cells expressing GFP.

FIGS. 19(a-b) illustrate (a) Representative FMT images show the accumulation of the RGD-NC particles in the liver and lungs of healthy and metastasis-bearing mice at 30 min post-injection. In the animal with metastases, hot spots with a significantly elevated concentration of the particles are indicated in the liver and spleen as ROI-1 and ROI-2, respectively. (b) Graph showing quantification of the fluorescence signal obtained from the FMT images of a group of healthy mice and a group of metastatic mice 30 min after injection of RGD-NC particles (data presented as mean±standard deviation). The signal of the hot spots in the lungs and liver of the metastatic group was compared to the average signal of these organs in the healthy group (n=6 animals per group).

FIGS. 20(a-c) illustrate: (a) Coronal T2-weighted images of the liver of a metastatic mouse before and 45 min after injection of the RGD-NC nanoparticles. In the 45-min post-injection image, the yellow arrows show micrometastases of about 0.5 mm in size with increased contrast enhancement. (b) Coronal T2-weighted images of the liver of a normal mouse 45 min after injection of the RGD-NC nanoparticles. (c) Plots showing the time-course of the MR signal intensity in the liver 'hot' spots was quantitatively evaluated. The absolute MR signal intensity in the metastatic lesions and the healthy liver was measured in manually drawn ROIs. The signal intensity in the hot spots or the entire healthy liver was normalized to the signal of an adjacent muscle (scale: 0-1). Since lower values indicate greater contrast in T2 images, normalized intensity values of 0 and 1 correspond to maximum and minimum contrast, respectively, compared to the pre-contrast intensity values (data presented as mean±standard deviation; n=3; each metastatic animal exhibited 2-4 hot spots; *P<0.05).

FIGS. 21(a-h) illustrate: (a) Fluorescence image of a histological section of the left lobe of the liver (5× magnification; blue: nuclear stain (DAPI); green: 4T1 cancer cells (GFP)). Images of entire histological sections of the organs were obtained using the automated tiling function of the microscope. (b-c) Fluorescence images of the location of metastatic cancer cells is shown with respect to endothelial cells and expression of αvβ3 integrin in the same histological section (10× magnification; green: 4T1 cancer cells; red: endothelial cells; blue: $α_vβ_3$ integrin). (d-f) Fluorescence images of the RGD-NC particles accumulated in locations of 4T1 cells that expressed αvβ3 integrin (10× magnification; blue: DAPI; green: 4T1 cancer cells; yellow: $α_vβ_3$ integrin; red: RGD-NC). (g-h) Fluorescence and bright field microscopy was performed on histological sections stained with hematoxylin-eosin showing the colocalization of RGD-NC and cancer cells and their relative anatomical location in the liver.

FIGS. 22(a-e) illustrate: (a-b) Fluorescence images showing the colocalization of fluorescently-tagged RGD-NC particles and metastatic cancer cells is shown in the same histological section (5× magnification; green: 4T1 cancer cells; red: RGD-NC; blue: DAPI). (c-e) Fluorescence images showing the location of RGD-NC particles is shown with respect to metastatic cancer cells and expression of αvβ3 integrin in the same histological section.

FIGS. 23(a-b) illustrate: FMT images of a mouse metastasis 1 hour post-injection a cocktail of (a) dual ligand-NC and (b) RGD-NC and EGFR-NC.

FIGS. 24(a-b) illustrate: (a) Bioluminescence images of Luc-4t1 cells of metastasis in metastasis bearing mice before and 3 days after RGD-DOX-NC treatment without radiofrequency (RF) and with RF. (b) Plot showing quantitative assessment of the progress of each metastatic tumor by measuring time-course of the BLI signal of each metastasis.

DETAILED DESCRIPTION

Figure 1:
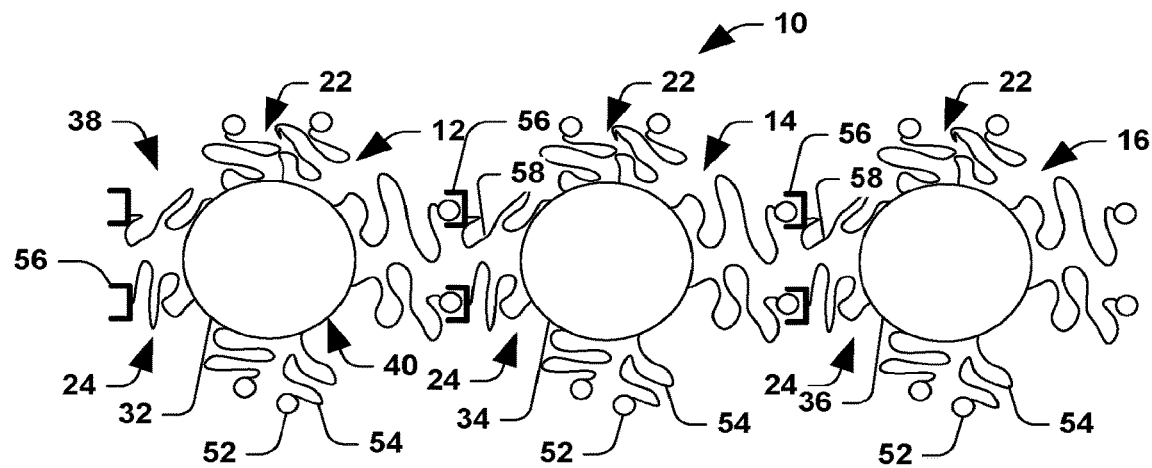
FIG. 1 is schematic illustration of a nanochain in accordance with one embodiment.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the term "imaging agent" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "targeting moiety" can refer to a molecule or molecules that are able to bind to and complex with a biomarker. The term can also refer to a functional group that serves to target or direct a therapeutic agent or anti-cancer agent to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

This application relates to a multi-component nano-scale chain (i.e., nanochain) that can be used for diagnostic and therapeutic applications. The nanochain can be linear or substantially linear and have an oblate nano-scale or high-aspect ratio shape with a length less than about 200 nm (e.g., about 100 nm to about 150 nm) and a width less than about two times the length of the nanochain (e.g., less than about three times or less than about four times the length of the nanochain). For example, the width of the nanochain can be about 50 nm or less, for example, about 10 nm to about 40 nm for a nanochain with a length of about 100 nm to about 150 nm. The oblate shape of the nanochain allows the nanochain when administered to a subject to have prolonged circulation in the subject compared to administration of nanoparticles alone. Advantageously, contrary to nanoparticle spheres that move along the center of a vessel in microcirculation, the oblate-shaped nanochains described herein can drift laterally in circulation moving in close proximity to the endothelium. This allows the nanochain to interact with vessel walls to, for example, target vascular specific biomarkers or extravasate through leaky tumor endothelium in tumor interstitium.

The nanochains described herein can be used in diagnostic, therapeutic, and/or theranostic applications to deliver therapeutic agents and/or imaging agents to cells and/or tissue of a subject as well as actively target cells and/or tissue of a subject upon systemic administration (e.g., intravenous, intravascular, intraarterial infusion) of the nanochains to the subject. The nanochains can also be remotely activated with a remote energy source to selectively release therapeutic agents and/or imaging agents to targeted cells and/or tissue of the subject.

FIG. 1 illustrates a linear multi-component nanochain 10 in accordance with an embodiment of the application. The linear nanochain 10 has an oblate shape and a length of about 100 nm to about 150 nm and a width of about 10 nm to about 50 nm. The nanochain 10 includes three nanoparticles 12, 14, and 16 that are linked together to form the nanochain 10. Although a linear nanochain 10 with three nano-particles is illustrated, the nanochain can include, for example, four, five, six, or more nanoparticles linked together.

Each nanoparticle 12, 14, and 16 of the nanochain 10 can have an asymmetric surface chemistry defined by first linkers 22 and second linkers 24 asymmetrically disposed on the surfaces 32, 34, and 36 of the nanoparticles 12, 14, and 16 of the nanochain 10. The nanoparticles 12, 14, and 16 are linked by binding and/or complexing of the first linkers 22 and second linkers 24 asymmetrically disposed on the nanoparticles 12, 14, and 16.

The nanoparticles 12, 14, and 16 used to form the nanochains 10 can include any material that can be formed into a nanoparticle (or nanoshell or nanomembrane) with nanoscale dimensions (e.g., about 1 nm to about 50 nm) and to which can be provide an asymmetric surface chemistry. Examples of nanoparticles can include metal nanoparticles, lipidic nanoparticles, polymer nanoparticles, liposomes, dendrimer, quantum dots, and/or combinations of these materials. In some embodiments, the nanoparticles can be optically or magnetically detectable. In other embodiments, intrinsically fluorescent or luminescent nanoparticles, nanoparticles that comprise fluorescent or luminescent moieties, plasmon resonant nanoparticles, and magnetic nanoparticles are among the detectable nanoparticles that can be used.

In general, the nanoparticles 12, 14, and 16 can have dimensions small enough to allow the nanochain to be systemically administered to a subject and targeted to cells and tissue of the subject. In some embodiments, the nanoparticles can have a size that facilitates extravasation of the nanochain in cancer therapy or diagnosis. Typically, the nanoparticles can have a longest straight dimension (e.g., diameter) of about 50 nm or less. In some embodiments, the nanoparticles have a diameter of 50 nm or less. Smaller nanoparticles, e.g., having diameters of 30 nm or less, e.g., about 1 nm to about 30 nm or about 1 nm to about 5 nm, are used in some embodiments.

The nanoparticles of the nanochain may be uniform (e.g., being about the same size) or of variable size. Particles may be any shape (e.g., spherical or rod shaped), but are preferably made of regularly shaped material (e.g., spherical). In some embodiments, the geometry or structure of the nanoparticles can incorporate the functional capabilities of nanotip, nanosphere, and nanoring geometries. Other geometries can include spherical, circular, triangle, quasi-triangle, square, rectangular, hexagonal, oval, elliptical, rectangular with semi-circles or triangles and the like. Selection of suitable materials and geometries are known in the art.

In some embodiments, the nanoparticles can include quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but not limited to, Ag, Au, Cu, Al, Fe, Co, Ni, Ru, Rh, Pd, and Pt or oxides thereof. In another embodiment, the metal comprises Fe or iron oxide. A further surface functional layer can be added or formed in combination with a metal core material. Such functional layers can include, but are not limited to, Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, tin oxide, antimony oxide, iron oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, and the like. In some embodiments, the metal core can be Au, Ag, Fe, Ti, Ni, Cr, Pt, Ru, NiCr alloy, NiCrN, PtRh alloy, CuAuCo alloy, IrRh alloy and/or WRe alloy. The metals used should be biocompatible.

In some embodiments, the nanoparticle can be a magnetic nanoparticle. "Magnetic particles" refers to magnetically responsive particles that contain one or more metals or oxides or hydroxides thereof. Nanochains including optically detectable metal nano-particles or quantum dots can be detected in vivo upon systemic administration to a subject using magnetic resonance imaging (MRI), magnetic resonance spectroscopy (MRS), nuclear magnetic resonance imaging (NMR), multimodal imaging, fluorescent, positron emission tomography (PET), near infrared (NIR) imaging, X-ray imaging, and computed tomography (CT).

In other embodiments, the nano-particles can include lipidic nanoparticles, polymer nanoparticles, liposomes, and/or dendrimers with a membrane, shell, or surface that is formed from a naturally-occurring, synthetic or semi-synthetic (i.e., modified natural) material. In some embodiments, the lipidic nanoparticles or liposomes can include a membrane or shell that is formed from a naturally-occurring, synthetic or semi-synthetic material that is generally amphipathic (i.e., including a hydrophilic component and a hydrophobic component). Examples of materials that can be used to form the membrane or shell of the lipidic nanoparticle or liposome include lipids, such as fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane or shell of the lipidic nano-particle or liposome, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl) methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

The first linkers 22 and second linkers 24 asymmetrically disposed on the nanoparticle can define respectively a first face 38 (or first partially modified area) and a second face 40 (or second partially modified area) of the nanoparticles 12, 14, and 16. The first face 38 and the second face 40 define by the first linkers 22 and second linkers 24 can be opposite regions or areas of the surface of nanoparticle.

The first linkers 22 and second linkers 24 can be of any suitable length and contain any suitable number of atoms and/or subunits to provide an oblate and/or liner nanochain. The linkers can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the first linker 22 can include a first polymer tether 50 and a first end group 52. The second linker 24 can include a second polymer tether 54 and second end group 56. The first end groups 52 and the second groups 56 of the first linkers 22 and second linkers 24 disposed on separate nanoparticles 12, 14, and 16 can bind or complex to link the separate nanoparticles.

The first polymer tethers 50 of the first linkers 22 and the second polymer tether 56 of the second linkers 24 can be formed of any flexible polymer chain that can be bound to and extend from the nanoparticles and provided with a first end group 52 or second group 56. In some embodiment, the first polymer tether 50 and the second polymer tether 54 can include biocompatible polymer, such as polyethylene glycol (PEG) (MW about 500 to 50,000 and 1000 to 10,000); polypropylene glycol (MW about 500 to about 50,000), dextran, and derivatives such as amino-dextran and carboxy-dextran, and polysaccharides. The first polymer tether 50 and the second polymer tether 54 can be attached directly or indirectly to the nanoparticles and/or a coating layer disposed on the nanoparticle.

Polymers used to coat the nanoparticles include amphiphilic polymers, detergent and/or a lipid structure including detergent derivatives and lipid derivatives. The amphiphilic polymer can include, but is not limited to hydrocarbons and DTPA modified poly(acrylic acid), poly(maleic acid), poly (maleic anhydride), and the like. The detergents can include, but are not limited to, AOT, brij family, Igepal family, triton family, SDS, or derivatives of each. In particular, the detergents can include, dioctyl sulfosuccinate sodium salt, polyethylene glycol dodecyl ether, (octylphenoxy) polyethoxyethanol, octylphenyl-polyethylene glycol, t-octylphenoxypolyethoxyethanol, polyethylene glycol tert-octylphenyl ether, 4-(1,1,3,3-tetramethylbutyl)phenyl-polyethylene glycol, dodecyl sulfate sodium salt, or glycolic acid ethoxylate octyl ether. Further, the block copolymer can include lipids such as, but not limited to, lipid-PEG, natural lipids, synthetic lipids, sphingolipids, or derivatives of each.

In particular, the block copolymer can include an ABC triblock structure having a poly-butylacrylate segment, a poly-ethylacrylate segment, or a poly-methacrylic acid segment, for example. The block copolymer can include a diblock and/or triblock copolymer having two or more different poly-aliphatic-acrylate segments. In addition, the block copolymer can include a diblock and/or triblock copolymer having two or more poly-alkyl-acrylate segments.

The first polymer tether 50 and the second polymer tether 54 can be linked to the nanoparticle directly or indirectly by any means. For example, the first polymer tether and the second polymer tether can be linked to the nanoparticle using a covalent link, a non-covalent link, an ionic link, and a chelated link, as well as being absorbed or adsorbed onto the nanoparticles. In addition, the first polymer tether and the second polymer tether can be linked to the nanoparticles through hydrophobic interactions, hydrophilic interactions, charge-charge interactions, π-stacking interactions, combinations thereof, and like interactions.

The first end groups 52 and the second end groups 56 of the first polymer linkers 22 and the second polymer linkers 24 can include functional groups that are reactive with, complex with, or bind to each other to allow the first linkers 22 and second linkers 24 of separate nanoparticles to bind and link the separate nanoparticles using solid phase synthesis techniques. The functional groups can include, for example, amines, carboxylic acids, hydroxyls, thiols, and combinations thereof that can potentially react with each other to link separate nanoparticle. In one embodiment, the first end group 52 can comprise an amine group and the second end group 56 can comprise a thiol group that is reactive with the amine group.

The nanochains can be prepared using solid-phase synthesis in which each asymmetric nanoparticle is serially added to form the nanochain. Firstly, the chemical properties of a nanoparticle are defined by controlling the topology of functional groups on its surface. Assuming attachment of a nanoparticle decorated with one type of functional group on a solid surface via a cleavable crosslinker, liberation via cleavage can result in a new functional group located at the portion of the nanoparticle's surface that interacted with the solid surface. For example, thiolytic cleavage of a crosslinker containing a disulfide bridge will create a thiol group. More specifically, solid-phase chemistry can be used to partially convert amine groups on the surface of desired nanospheres into thiols resulting in a particle with asymmetric surface chemistry (ASC). Accordingly, in a first step, nanoparticles with a first linker or function group can be linked to a solid support via a crosslinker containing a cleavable bridge. Liberation of the nanoparticle by cleavage of the bridge can create a second functional groups or second linkers on a portion of the nanoparticle's surface that interacted with the solid support resulting in a nanoparticle with two faces, one displaying only the first linkers and the other only the second linkers. In a second step, employing solid-phase chemistry and step-by-step addition of nanoparticles, the two unique faces on the same nanoparticles can be used as fittings to assemble them into nanoparticle nanochains.

In some embodiments, the nanochains can additionally or optionally include at least one targeting moiety that is capable of targeting and/or adhering the nanochain to a cell or tissue of interest. The targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproplyl]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, a targeting moiety as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chmokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting moiety can be targeting peptide comprising an EGF peptide. The EGF peptide may comprise the amino acid sequence YHWYGYTPQNVI-amide (SEQ ID NO: 1). The peptide may be synthesized by any method known in the art. For example, the EGF peptide may be synthesized manually using Fmoc protected amino acids (Peptides International, Louisville, Ky.) on rink-amide CLEAR resin (Peptides International, Louisville, Ky., 100-200 mesh size, 0.4 milliequivalents/gram).

In other embodiments, the targeting moiety can include cyclic tripeptide arginine-glycine-aspartic acid (cRGD) (SEQ ID NO: 2), which is ligand for vascular targeting and metastasis.

In still other embodiments, the targeting moiety may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the composition to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

The targeting moiety can be coupled to nanoparticles of the nanochain using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the nanoparticles can include multiple types of targeting moieties and the spacing and location of the targeting moieties on each nanoparticle can be controlled to facilitate delivery, targeting, and/or therapeutic efficacy of the nanochain. In other embodiments, the targeting moieties on the surface of the nanoparticles and the spacing between the nanoparticles can be controlled to facilitate targeting of the nanoparticles to cells of a subject.

In other embodiments, the nanochain can include imaging agents (or detectable moieties) and/or therapeutic agents that are encapsulated by (e.g., within liposome, lipidic nanoparticle, or polymer nanoparticle), contained in (e.g., polymer nanoparticles or dendrimers), or conjugated to the nanoparticles. Therapeutic agents encapsulated by, contained in, and/or linked to the nanoparticles can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease or injury in a subject. Examples of therapeutic agents include, but are not limited to anti-cancer agents, anti-proliferative agents, and chemotherapeutic agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and nanochain in the subject. Examples of imaging agents include, but are not limited to: radionuclides, fluorescent dyes, chemiluminescent agents, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the imaging can an include MRS/MRI radiolabel, such as gadolinium, 19F, 13C, that is coupled (e.g., attached or complexed) with the nanochain using general organic chemistry techniques. The imaging agent can also include radiolabels, such as 18F, 11C, 75Br, or 76Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, N Y 1986) the contents of which are hereby incorporated by reference. The imaging can also include 123I for SPECT.

The imaging agent can further include known metal radiolabels, such as Technetium-99m (99mTc). Preparing radiolabeled derivatives of Tc99m is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

In some embodiments, the therapeutic agent can be an anti-cancer agent or anti-proliferative agent that is encapsulated by, contained in, and/or linked to the nanoparticles. The phrase "anti-cancer agent" or "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms. There are a large number of anti-proliferative agent agents available in commercial use, in clinical evaluation and in pre-clinical development, which can be administered in combination with the nanochain.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of antimetabolite antineoplastic agents include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

Examples of alkylating-type anti-proliferative agents include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

Miscellaneous antineoplastic agents include, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, EULEXIN, Cell Pathways EXISULIND (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In some embodiments, the therapeutic agents can be loaded into and/or onto the nanoparticles by encapsulation, absorption, adsorption, and/or non-covalent linkage of the therapeutic agent to or within the nanoparticle. The amount of therapeutic agent loaded onto or in the nanoparticle can be controlled by changing the size of the nanoparticle or the composition of the nanoparticle.

In some embodiments, release of the therapeutic agent from the nanoparticle of the nanochain can occur by desorption, diffusion through the polymer or lipid coating, or polymer or lipid wall, nanoparticle erosion, and/or disruption of the nanoparticle structure, which can all be controlled by the type of the nanoparticle, i.e., having it become swollen or degradable in the chosen microenvironment.

In other embodiments, release of the therapeutic agent or imaging agent from the nanoparticle of the nanochain can be remotely triggered by a remote energy source that supplies energy to the nanochain effective to release the therapeutic agent or imaging agent from the nanoparticle. In one embodiment, the multi-component nanochain can include at least two metal nanoparticles and a liposome, lipidic nanoparticle, or polymer nanoparticle linked together to form the nanochain. The liposome, lipidic nanoparticle, or polymer nanoparticle can encapsulate or contain the therapeutic agent (e.g., chemotherapeutic agent, such as doxorubicin). The metal nanoparticles of the nanochain can be responsive to energy, from a remote source that is effective to release the therapeutic agent from the liposome, lipidic nanoparticle, or polymer nanoparticle after administering the nanochain to a subject. The remote source can be external or remote from a subject, which allows non-invasive remote release of the therapeutic agent to the subject. Advantageously, a nanochain that allows remote release of the therapeutic agent, such as a chemotherapeutic agent (e.g., doxorubicin) can target or be targeted to specific cells or tissue of subject, such as tumors, cancers, and metastases, by systemic administration (e.g., intravenous, intravascular, or intraarterial infusion) to the subject and once targeted to the cells or tissue remotely released to specifically treat the targeted cells or tissue of subject (e.g., tumors, cancers, and metastasis). Targeting and selective release of the chemotherapeutic agents to malignant cancer metastases allows treatment of such metastases using chemotherapeutics, which would provide an otherwise neglible effect if not targeted and remotely released using the nanochains described herein.

In some embodiments, mild radiofrequency (RF) energy from a remote RF energy source can generate a magnetic field that can be used to release a therapeutic agent or imaging agent from liposome, lipidic nanoparticle, or polymer nanoparticles that are linked to a linear nanochain of metal nanoparticles. The liposome, lipidic nanoparticle, or polymer nanoparticle can have a membrane or shell that encapsulates or contains a therapeutic agent or imaging agent. The liposome, lipidic nanoparticle, or polymer nanoparticle can readily release the therapeutic agent or imaging agent upon mechanical disruption of the membrane or shell. The linked metal particles of the nanochain can be responsive to RF energy from a remote RF energy source and act as a mechanic transducer to mechanically resonate or oscillate upon application of RF energy from the energy source. Application of mild RF energy from RF source can rapidly release the therapeutic agent or imaging agent from the liposome, lipidic nanoparticle, or polymer nanoparticle membrane or shell due to defects in the membrane or shell cause by oscillation of the metal nanoparticle tail. The mild RF energy applied to the nanochain can be that amount effective cause the metal nano-particles to mechanically resonate or oscillate at an amount or level effective to disrupt liposome, lipidic nanoparticle, or polymer nanoparticle membrane or shell and release the therapeutic agent from the liposome, lipidic nanoparticle, or polymer nanoparticle without causing significant heating (e.g., greater than 1° C., 2° C., 3° C., or 5° C.) around the nanochain when administered to a subject.

Figure 2:
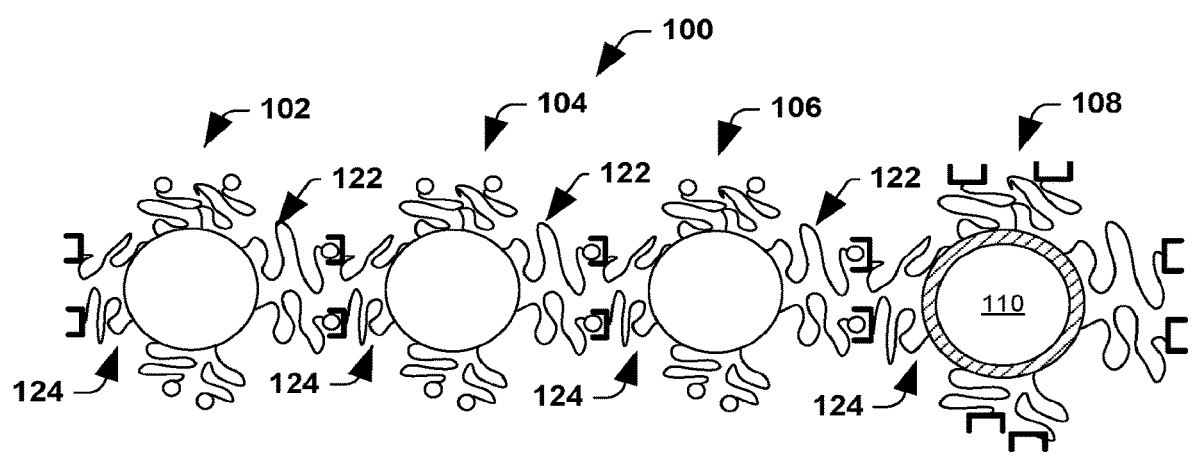
FIG. 2 is a schematic of a nanochain in accordance with another embodiment.

By way of example, FIG. 2 illustrates a linear multi-component nanochain 100 that includes three iron oxide three nanoparticles 102, 104, and 106 that are linked to liposome 108 that contains a therapeutic agent 110 (e.g., chemotherapeutic agent). The iron oxide nanoparticles 102, 104, and 106 can have a nominal or average diameter of about 10 nm to about 30 nm (e.g., about 20 nm) and the liposome 108 can have a nominal diameter of about 20 nm to about 40 nm (e.g., about 30 nm). The nanochain 100 can be linear or substantially linear and have oblate nano-scale shape with a length of about 100 nm to about 150 nm and a width of about 10 nm to about 50 nm. The oblate shape of the nanochain 100 allows the nanochain when administered to a subject to have prolonged circulation in the subject compared to administration of the nanoparticles alone.

Each iron oxide nanoparticle 102, 104, and 106 of the nanochain 100 can have an asymmetric surface chemistry defined by first linkers 122 and second linkers 124 asymmetrically disposed on the surfaces of the iron oxide nanoparticles 102, 104, and 106 of the nanochain 100. The iron oxide nanoparticles can be linked by binding and/or complexing of the first linkers 122 and second linkers 124 asymmetrically disposed on the iron oxide nanoparticles. The liposome 108 containing the therapeutic agent 110 can include second linkers 124 that allow the liposome 108 to bind to first linkers 122 of a terminal iron oxide nanoparticle 106 of the linked iron oxide nanoparticles.

The nanoparticles can also include one or multiple types of targeting moieties (not shown) that are linked to the nanoparticles and/or liposome and allow the nanochain 100 to be targeted to, for example, a tumor, cancer cell, or metastasis. Examples of targeting moieties include an integrand targeting peptide and EGFR targeting peptide.

Upon administration of the nanochain 100 to a subject by, for example, intravascular administration, the nanochain can target the tumor, cancer, or metastases being treated. The nanochain can be imaged by, for example, magnetic resonance imaging or computed tomography, to confirm localization and targeting of the nanochain to the tumor or cancer cells. The nanochain targeted to the tumor, cancer, or metastases can be applied mild RF energy from a remote RF energy that is external to the subject being treated to mechanically resonate or oscillate the iron oxide nanoparticle tail of the nanochain and rapidly release the therapeutic agent from the liposome membrane or shell due to defects in the membrane or shell cause by oscillation of the iron oxide nanoparticle tail.

It will be appreciated that other remote energy sources can be used to release the therapeutic agent or imaging agent from the nanochain and that the selection of the energy source will depend at least in part on the nanoparticles used to form the nanochain. For example, the nanochain can include a chain of metal nanoparticles, such as gold nanoparticles, that are linked to a thermosensitive liposome, lipidic nanoparticle, or polymer nanoparticle that contains or encapsulates a therapeutic agent or imaging agent. Electromagnetic radiation can be applied to the nanochain after administration to a subject from a remote energy source, such as a remote near infrared laser, to cause the gold nanoparticles to heat to a temperature (e.g., about 40 C to about 45 C) effective to disrupt the thermosensitive liposome, lipidic nanoparticle, or polymer nanoparticle and release the therapeutic agent from liposome, lipidic nanoparticle, or polymer nanoparticle. Gold nanoparticles can efficiently convert photons from the remote energy source to heat. The remote energy source can be, for example, a minimally invasive laser that can be inserted in vivo in the subject being treated or positioned external or ex vivo the subject. The energy from laser can be in the near infrared range to allow deep radiation penetration into tissue and remote release of therapeutic agent or imaging agent.

In some embodiments, the nanochains described herein can be formulated in a pharmaceutical composition. Formulation of pharmaceutical composition for use in the modes of administration noted below (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

For example, pharmaceutical compositions can contain can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose.

Examples of formulations for parenteral administration can include aqueous solutions of the composition in water-soluble form, for example, water-soluble salts and alkaline solutions. Especially preferred salts are maleate, fumarate, succinate, S,S tartrate, or R,R tartrate. In addition, suspensions of the composition as appropriate oily injection suspensions can be administered. Aqueous injection suspensions can contain substances that increase the viscosity of the suspension, such as sodium carboxymethyl cellulose, sorbitol and/or dextran. Optionally, the suspension may also contain stabilizers.

Formulations for topical administration to the skin include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

In some embodiments, the nanochains described herein can be used in a method for treating a disorder in a subject. The disorder can include diseased cells. The cells can include a diseased cell or healthy cell that is derived from, or a part of, various tissue types, such as neuronal tissue (including both neuron and glia), connective tissue, hepatic tissue, pancreatic tissue, kidney tissue, bone marrow tissue, cardiac tissue, retinal tissue, intestinal tissue, lung tissue, endothelium tissue, cartilage, skeletal muscle, cardiac muscle, other cardiac tissue that is not muscle, smooth muscle, bone, tendon, ligament, adipose tissue and skin. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc.

In some embodiments, a therapeutically effective amount of the nanochains can be administered in vivo to a subject to treat the subject. The nanochains may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. For example, the nanochains may be introduced into the central nervous system by any suitable route, including intraventricular injection, intrathecal injection, or intraventricular injection via an intraventricular catheter that is attached to a reservoir.

The nanochains can also be delivered systematically (e.g., intravenously), regionally, or locally (e.g., intra- or peritumoral injection) by, for example, intraarterial, intratumoral, intravenous, parenteral, intrapneural cavity, topical, oral or local administration, as well as subcutaneous, intrazacheral (e.g., by aerosol), or transmucosal (e.g., voccal, bladder, vaginal, uterine, rectal, nasal, mucosal). If delivery of the nanochains to the brain is desired, the targeted nanoparticles can be injected into an artery of the carotid system of arteries (e.g., occipital artery, auricular artery, temporal artery, cerebral artery, maxillary artery etc.). As discussed above, the nanochains can be formulated as a pharmaceutical composition for in vivo administration.

The nanochains can be administered to the subject at an amount effective to provide a desired result(s) and to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The nanochains can be administered in a variety of unit dosage forms, depending upon the particular cell or tissue being treated, the general medical condition of each subject, the method of administration, and the like. Details on dosages are well described in the scientific literature. The exact amount and concentration of the targeted nanochains, or the "effective dose", can be routinely determined (e.g., by a medical practitioner). The "dosing regimen" will depend upon a variety of factors, such as whether the cell or tissue to be treated is disseminated or local, the general state of the subject's health, the subject's age, and the like. Using guidelines describing alternative dosing regimens, e.g., from the use of other agents and compositions, the skilled artisan can readily determine by routine trials the optimal effective concentrations of the composition.

In some embodiments, the nanochains described herein can be use with in vivo imaging methods where detection and imaging of cells or tissue cannot readily be performed with traditional optical detection or imaging techniques. These methods can include, for example, endovascular detection, cancer and metastasis imaging, infection or inflammation imaging, imaging of cell and tissue apoptosis, localization of neurologic pathways involved in chronic pain, and localization of epilepsy foci. It will be appreciated that the nanochains can be used in other in vivo methods as well as intraoperative procedures.

In each method, a plurality of the nanochains can be delivered to the cells or tissue of the subject in vivo by administering an effective amount or concentration of the nanochains to the subject. By effective amount or concentration of the nanochains, it is meant an amount of the nanochains that are effective for detecting and imaging the target cells or tissue. As apparent to one skilled in the art, such an amount will vary depending on factors that include the amount of tissue to be imaged, the rate of contact of the nanochains with the tissue, any abnormalities of the tissue that may affect the efficiency of the nanochains contacting or binding to the tissue.

In some embodiments, the nanochains can be administered to the subject by venous (or arterial) infusion. In venous infusion, an effective amount or concentration of the nanochains administered to subject can be that amount or concentration that is detectable in the tissue or cells after sequestration of the nanochains in the liver, spleen, and lymph nodes. Optionally, the nanochains can be administered to the subject by directly injecting the nanochains into cells or tissue of the area being identified or an area proximate or peripheral to the area being identified. Direct injection of the nanochains can be performed by using, for example, a syringe.

In other embodiments, the nanochains can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external.

At least one image of the ROI can be generated using an imaging modality once the nanochains localize to the ROI. The imaging modality can include one or combination of known imaging techniques capable of visualizing the nanochains. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET).

In one example, the nanochain can be detected with MRI and/or x-ray. MRI relies upon changes in magnetic dipoles to perform detailed anatomic imaging and functional studies. The electron dense core of nanoparticles of the nanochain, such as metal nanoparticles, can also make them highly visible on X-ray, monochromatic X-ray, computed tomography (CT) and ultrasound (US).

Optionally, the nano-particles of the nanochain can be modified to facilitate detection and imaging with MRI and CT as well as positron emission tomography (PET). For MRI applications, gadolinium tags can be attached to the shell and/or iron oxide can be as nanoparticles in the nanochain. For PET applications, radioactive tags can be attached to nanoparticles. For CT applications, iodide or other heavy metals can be attached to the nanoparticles to facilitate CT contrast.

It will be appreciated the nanochains will likely be most useful clinically when several imaging techniques or imaging followed by a medical or surgical procedure is used. In this way, the ability to use one agent for multiple imaging modalities is optimized making the nanochains cost-competitive with existing contrast agents.

For multimodal imaging applications, the nanochains can be administered to a subject and then preoperatively imaged using, for example, CT or MRI. After preoperative imaging, the nanochains can serve as optical beacons for use during surgery leading to more complete resections or more accurate biopsies. In surgical resection of lesions, the completeness of resection can be assessed with intra-operative ultrasound, CT, or MRI. For example, in glioma (brain tumor) surgery, the nanochains can be given intravenously about 24 hours prior to pre-surgical stereotactic localization MRI. The nanochains can be imaged on gradient echo MRI sequences as a contrast agent that localizes with the glioma.

In other embodiments, the nanochains can be administered to a subject to treat and/or image a neoplastic disease in subject. Neoplastic diseases treatable by the nanochains described herein can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells. The neoplastic disease can also include cancer and malignant cancer metastases.

A composition comprising the nanochains describe herein that includes an anti-cancer agent or anti-proliferative agent can be formulated for administration (e.g., injection) to a subject diagnosed with at least one neoplastic disorder. The nanochains can be formulated according to method as described above and include, for example, at least one therapeutic agent or imaging agent as well as targeting moiety to target the neoplastic cells or cancer cells.

The following examples are for the purpose of illustration only and are not intended to limit the scope of the claims, which are appended hereto.

Example 1

We exploited the engineerability of nanoparticles to shape them with defined geometrical and chemical properties. Firstly, the chemical properties of a nanosphere were defined by controlling the topology of functional groups on its surface. Assuming attachment of a nanosphere decorated with one type of functional group on a solid surface via a cleavable crosslinker, liberation via cleavage can result in a new functional group located at the portion of the nanosphere's surface that interacted with the solid surface. For example, thiolytic cleavage of a crosslinker containing a disulfide bridge will create a thiol group. More specifically, solid-phase chemistry was used to partially convert amine groups on the surface of iron oxide nanospheres into thiols (FIG. 3a) resulting in a particle with asymmetric surface chemistry (ASC). It should be noted that the ASC strategy described here provides exceptional flexibility in controlling the surface functionalization that can be employed to various types of nanoparticles (e.g., liposome, dendrimer, metal particle), since the synthetic method is carried out in aqueous environment and physiological pH.

Figure 3:
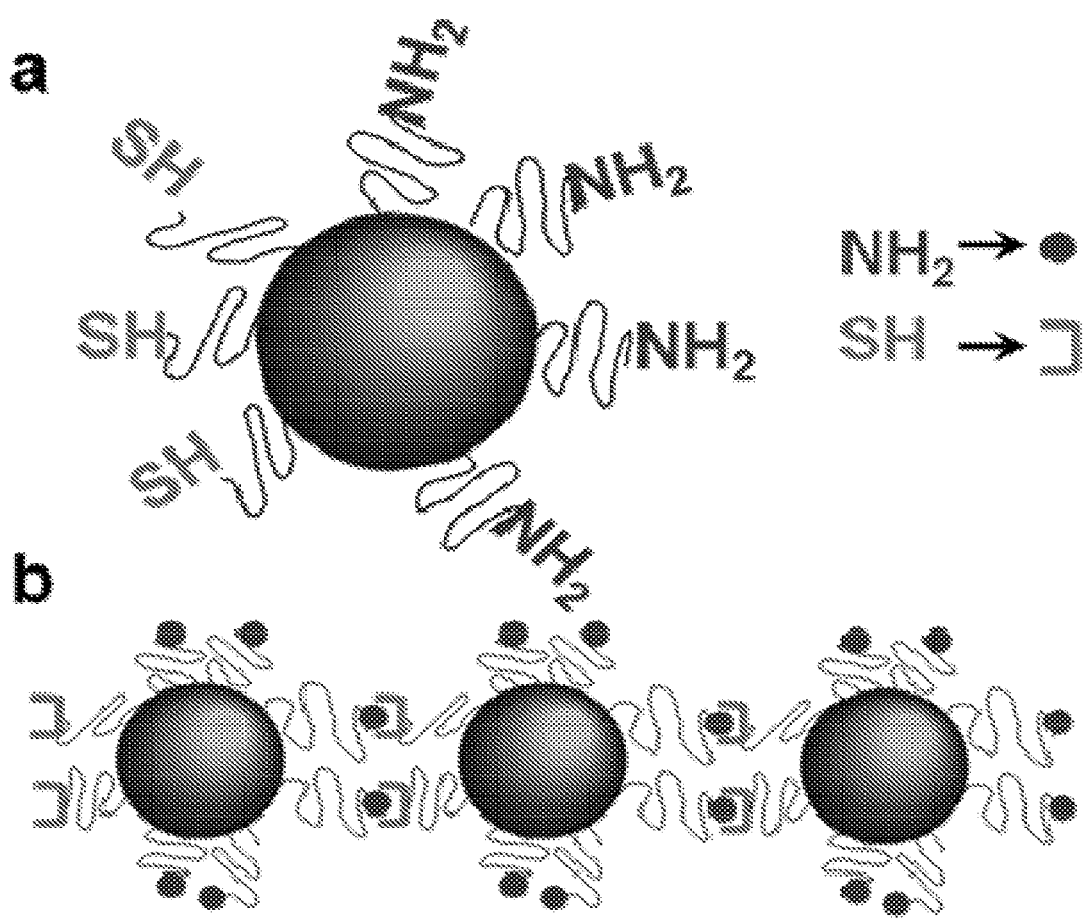
FIGS. 3(a-b) are schematic illustrations of (a) nanospheres with asymmetric surface chemistry (ASC) and (b) linear nanochains assembled from spheres with ASC.

Using a step-by-step addition of particles and solid-phase chemistry, the two unique faces on the nanoparticle served as fittings to assemble the particles with ASC into nanochains in a controlled manner (FIG. 3b). Different nanochains were synthesized and characterized consisting of nanospheres with different sizes. The nanochain exhibited a significant increase in T2 relaxivity compared to its constituting iron oxide nanospheres, which implies that they can be potent imaging agents for magnetic resonance imaging (MRI).

Figure 4:
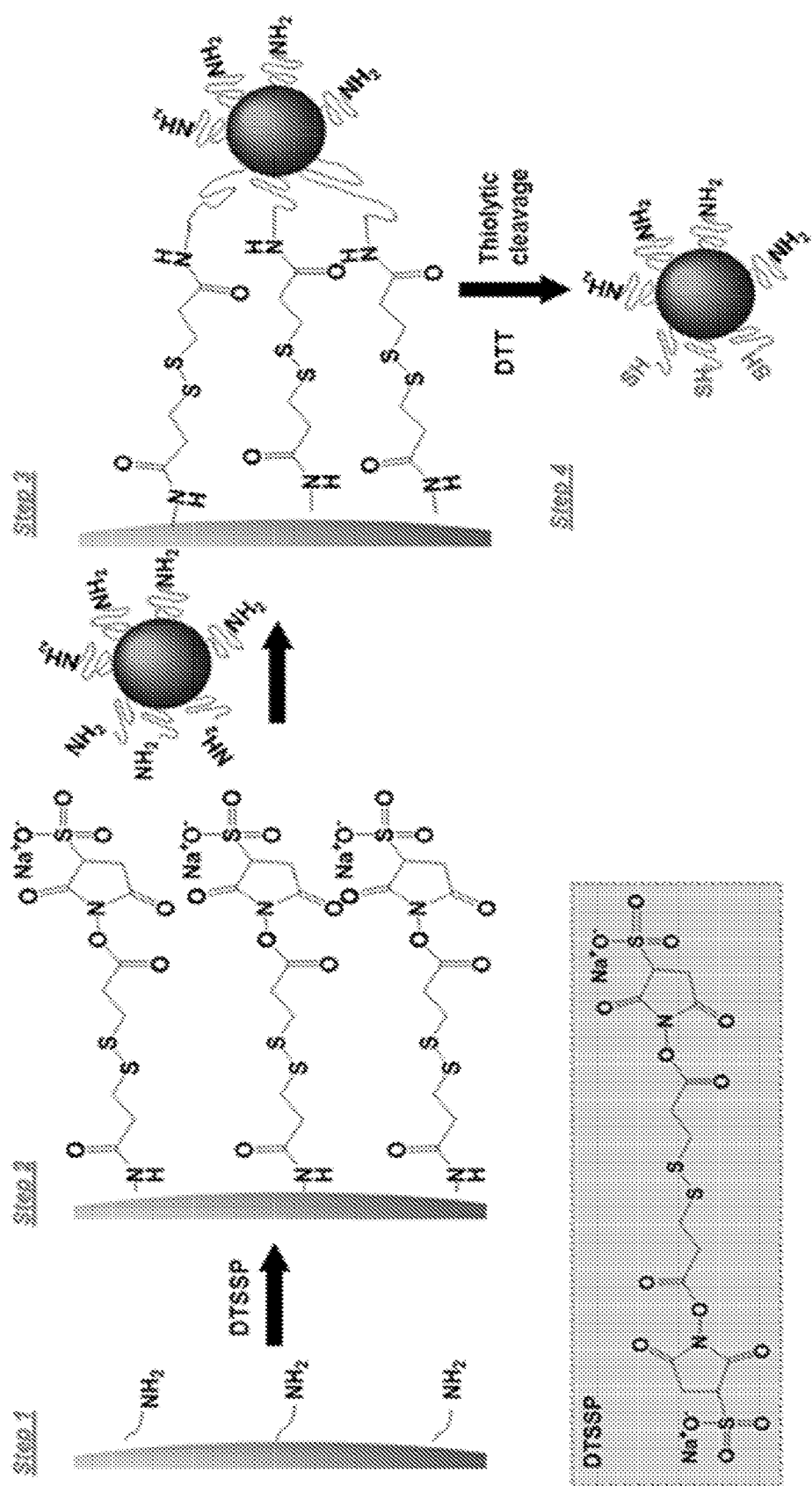
FIG. 4 illustrates a reaction of the fabrication of nanoparticles with asymmetric surface chemistry (ASC) showing the partial modification of the functional groups on a nanoparticle's surface using solid phase chemistry.

Materials and Methods
Synthesis and Characterization of Iron Oxide Nanospheres with Asymmetric Surface Chemistry Solid-phase chemistry was used to partially modify the surface functionality of iron oxide nanospheres. Various resins with high swellability in water, such as PEGylated resins with different densities of amine functional group, were used as solid support. In a typical experiment, 250 mg of CLEAR (Cross-Linked Ethoxylate Acrylate Resin) resin (Peptides International Inc, Louisville, Ky.) was placed in a fritted reactor and was washed and swollen in DMF followed by PBS. To attach nanospheres onto the resin, homobifunctional cleavable cross-linkers such as 3,3'-Dithiobis (sulfosuccinimidylpropionate) (0.32 mmol, DTSSP; Thermo Scientific, Rockford, Ill.) was introduced and allowed to react for 15 min as shown in FIG. 4. After the washing/drying cycle to remove unbound DTSSP, 1 mL of amine functionalized iron oxide nanospheres at 1 mg/mL iron concentration (Ocean Nanotech LLC, Springdale, Ark.) was added and mixed with resin beads. The iron oxide nanoparticles were prepared using iron oxide powder as the iron precursor, oleic acid as the ligand, and octadecene as the solvent. The particles were coated with a triblock polymer consisting of polybutylacrylate segment (hydrophobic), polymethacrylic acid (hydrophilic) and a hydrophobic carbon side chain. Amine-terminated Polyethylene Glycol polymer was conjugated onto the carboxyl groups of the surface of iron oxide nanoparticles. The conjugation reaction was allowed to proceed for 45 min with shaking. The nanosphere-resin complex was filtered and a washing/drying cycle was carried out to remove unbound nanospheres. Tris[2-carboxyethyl]phosphine (1.8 mmol, TCEP), a reducing agents, was added and kept for 45 min to cleave off the nanospheres from the resin. The suspension of iron oxide nanospheres with ASC was collected and dialyzed in 2000 Da MWCO membrane against PBS to remove the excess cleaving reagents.

To evaluate the topology of each functional group, we tagged the amines or the thiols on the nanosphere's surface with an excess of the appropriate gold probes (diameter of 1.4 nm; Nanoprobes, Yaphank, N.Y.) and then obtained transmission electron microscopy (TEM) images. More specifically, we incubated the nanosphere with a 10-molar excess of (1) NHS-functionalized gold probes, (2) maleimide-functionalized gold probes, (3) a mixture of NHS- and maleimide-functionalized gold probes, and (4) non-functionalized gold probes. Each suspension was then dialyzed against PBS using a 100 kDa MW cut-off membrane to remove unbound gold probes. TEM images were obtained using a Tecnai F30 instrument (FEI, Hillsboro, Oreg.) operated at 300 kV. The sample was prepared by dropping 3 μL of the nanosphere suspension onto a 400-mesh formvar carbon-coated copper grid, then the excess solution was blotted with a filter paper and the residual wetting layer was allowed to dry in air. The sizes and zeta potentials of the nanospheres were determined using a ZetaPALS dynamic light scattering system (Brookhaven Instruments, Holtsville, N.Y.). The concentration of iron was determined via ICP-OES (Optima 7000 DV; Perkin-Elmer, Waltham, Mass.).

Theoretical Analysis of the Asymmetry on the Nanosphere's Surface Chemistry

A number of factors govern the interaction of tethered ligands on the surface of a nanosphere and the functional groups on the surface of the resin. It has been shown that the distance of separation between two surfaces plays a significant role in binding of tethered ligand and receptor. As the nanosphere approaches the surface of the resin, the overall energy of the system starts decreasing resulting in the formation of amide bonds between the NHS ester of the resin and the primary amines on the nanosphere. This brings the nanosphere further closer to the resin and at a certain critical distance the overall energy of the system reaches minimum, causing the two surfaces to jump into spontaneous contact. Therefore, the maximum number of bonds is formed between the nanosphere and resin at this critical distance, also referred to as the binding distance. Using a combination of Monte Carlo simulations and diffusion reaction theory, we have demonstrated that the binding distance can be approximated as a function of the tether size.

Figure 6:
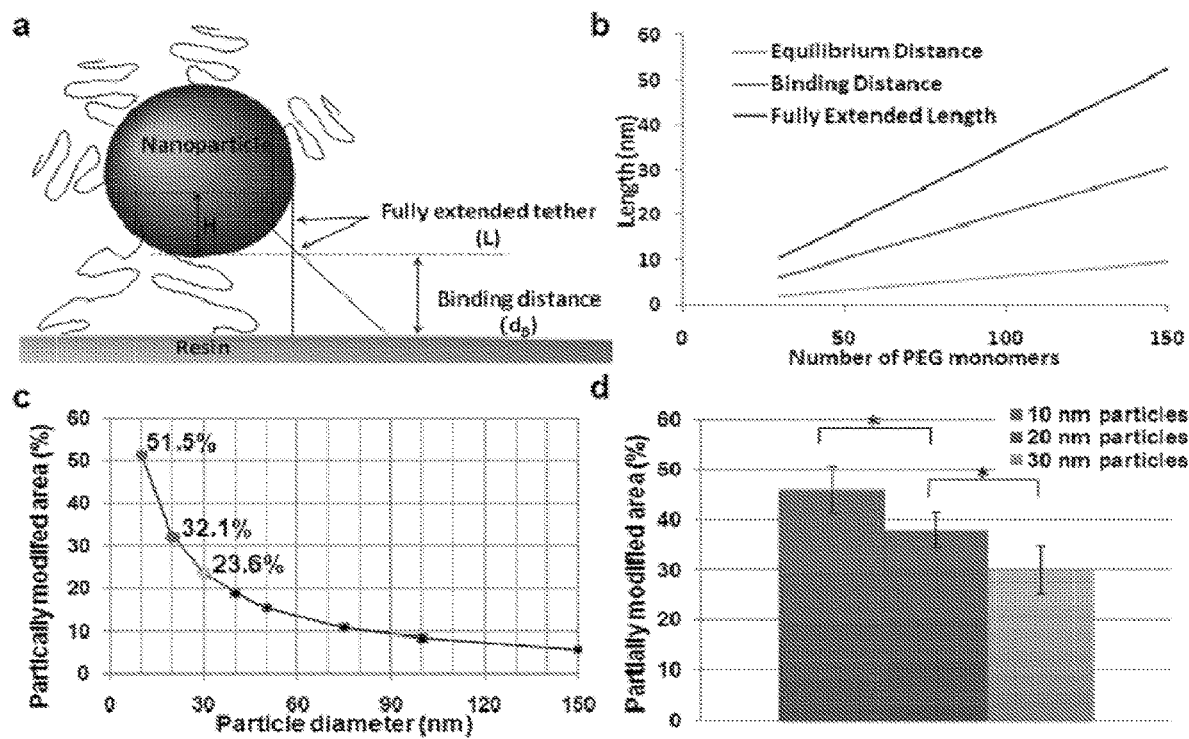
FIGS. 6(a-d) illustrate: (a) Schematic illustration of nanoparticle-resin surface binding. (b) Plot showing the length of PEG polymers with respect to tether interactions as a function of repeating monomers per PEG molecule. The equilibrium distance is defined as the distance corresponding to the Flory radius of a polymer. The binding distance is defined as the length of polymer at which maximum resin-ligand complexes are formed. The fully extended length corresponds to the maximum length of a polymer tether. (c) Plot showing theoretical estimation of the partially modified area (PMA) as a function of nanoparticle size. (d) Graph showing experimental measurement (n=3) of the portion of amines modified to thiols using NHS-functionalized Alexa-488 to fluorescently tag the amines (* indicates p<0.05; data presented as mean±standard deviation).

To study the effect of nanoparticle diameter and tether length on the surface modification of the nanosphere, the Partially Modified Area (PMA) was calculated similarly to Ghaghada. The PMA of the nanosphere is defined as the fraction of the surface that is capable of binding to the resin. The PMA is a function of tether size, ligand size, and nanosphere size. FIG. 6a illustrates the interactions between the nanosphere and the resin. The separation distance between the nanosphere of a radius R and the functional groups on the surface of the resin is given by the binding distance. Therefore, the separation distance is a function of tether length. Furthermore, it is assumed that the tether at the outermost end of the PMA forming a receptor-ligand complex is in a fully extended conformation. Therefore using simple geometry, the active area of a nanosphere can be calculated by the equation: $PMA=(2\pi RH)/(4\pi R^2)=H/(2R)=(L-d_B)/2R$, where R is the radius of the nanosphere, and H is given by $(L-d_B)$. L corresponds to the sum of ligand length and the maximum extended length of the tether, and $d_B$ is the binding distance.

Experimental Evaluation of the Asymmetric Presentation of Functional Groups on Nanospheres To determine the number of functional groups of each type, the amines on the nanosphere surface were reacted with the Alexa Fluor 488 NHS ester (Invitrogen, Carlsbad, Calif.). The amount of Alexa 488 on the surface of the nanospheres was analyzed by the fluorescence intensity using a fluorescence plate reader (Synergy HT; BioTek Instruments, Winooski, Vt.). In a typical experiment, iron oxide nanospheres with ASC (surface thiols and amines) and their parent iron oxide nanospheres (only surface amines) with different diameters (10, 20, 30 nm) were incubated with 10 molar excess of NHS-functionalized ALEXA FLUOR 488 over the surface amines for 2 hours in the dark with stirring. Each suspension was dialyzed against PBS using a 2000 Da MW cut-off membrane to remove unbound fluorescent tags. The purified solutions were pipetted into a 96-well plate and the intensity of the fluorescence signal was measured (excitation 480 nm, emission 520 nm). The exact iron concentration was assessed by ICP-OES after digesting all samples with concentrated $HNO_3$ acid. It was converted to particle concentration with the assumption that each particle was made of $Fe_3O_4$ and a 5.2 $g/cm^3$ density. The average fluorescence intensity of the nanospheres with ASC was compared to the amine-only-functionalized nanospheres of the same size to obtain the percentage of converted amines to thiols.

Synthesis of Linear Nanochains

Solid-phase chemistry was used to synthesize iron oxide nanochains. Initially, 250 mg of amine-functionalized CLEAR resin were reacted with DTSSP (0.32 mmol) for 15 min (step 1 in FIG. 7). After the washing/drying cycle to remove unbound DTSSP, 1 mL of nanospheres with ASC at 5 µg/mL iron concentration were added and mixed with resin beads (step 2). The conjugation reaction was allowed to proceed for 15 min with shaking. Nanosphere-attached resin was filtered and a washing/drying cycle was carried out to remove unbound particles. An excess amount of sulfo-NHS acetate was introduced and kept for 15 min to block the unreacted amine groups. The heterobifunctional crosslinker sulfosuccinimidyl 4[N-maleimidomethyl]cyclohexane-1-carboxylate (0.05 mmol, Sulfo-SMCC) was introduced and kept for 15 min After removing excess crosslinker, the next wave of nanospheres with ASC was introduced (step 3). This process was repeated until the desired length of the nanochain was obtained (step 4). Reducing agents such as DTT or TCEP were added and kept for 45 min to cleave off the nanochain from the resin (final step). The nanochain suspension was collected and dialyzed in 2000 Da MWCO membrane against PBS to remove the excess cleaving reagents. TEM analysis was carried out as described previously. The formation of covalent bonds between solid surface-nanosphere and sphere-sphere was characterized using FTIR spectroscopy. The infrared analyses were obtained using a Thermo Nexus 870 FTIR spectrometer with an attenuated total reflection (ATR) accessory. Spectra over the 4000-500 $cm^{-1}$ range were obtained by the co-addition of 64 scans with a resolution of 4 $cm^{-1}$. The exact iron concentration of the nanochain formulations was assessed by ICP-OES after digesting all samples with concentrated $HNO_3$ acid.

Relaxation Measurements

A Bruker Minispec Analyzer MQ60 was used for T2 measurements at 1.4 Tesla. A total of 300 µL of each sample were placed in a 0.6 mm sample tube and allowed to equilibrate to 40° C. All the measurements were made at 40° C. and each measurement was repeated four times to measure variations within the readings. T2 curves were obtained using the instrument's Carr-Purcell-Meiboom-Gill (CPMG) pulse sequence ($t_2$_cp_mb) with a recycle delay of 20 seconds and 200 data points were collected.

Results

Synthesis of Nanoparticles with Asymmetric Surface Chemistry

Solid phase synthesis was used to produce iron oxide nanospheres with ASC consisting of two areas with distinct functional group distribution (i.e. thiols and amine) as shown in FIG. 4. We used the CLEAR resin which is an amine-functionalized resin particle of 100 µm with a swelling in water of ~5.5 ml/g, and a substitution level of 0.72 mmol/g (manufacturer's product specifications sheet). Using a previously published method, we calculated 1.172× $10^9$ amines per bead of resin. As illustrated in FIG. 4, we used large excess of homobifunctional cleavable cross-linkers such as DTSSP to react all the amines on the resin. As a result, the solid-phase surface displayed multiple active sites available for binding to the upcoming nanospheres. Once the amine-functionalized iron oxide nanospheres were attached to the solid support via DTSSP, the disulfide bond in DTSSP could be easily cleaved with the addition of a mild reducing agent such as TCEP (or DTT). As a result of this cleavage, the portion of the nanosphere's surface that interacted with the solid support was decorated with thiol groups whereas the rest of the surface maintained its initial decoration of amine groups. We modified the surface of three iron oxide nanospheres with sizes of 10, 20, and 30 nm.

Figure 5:
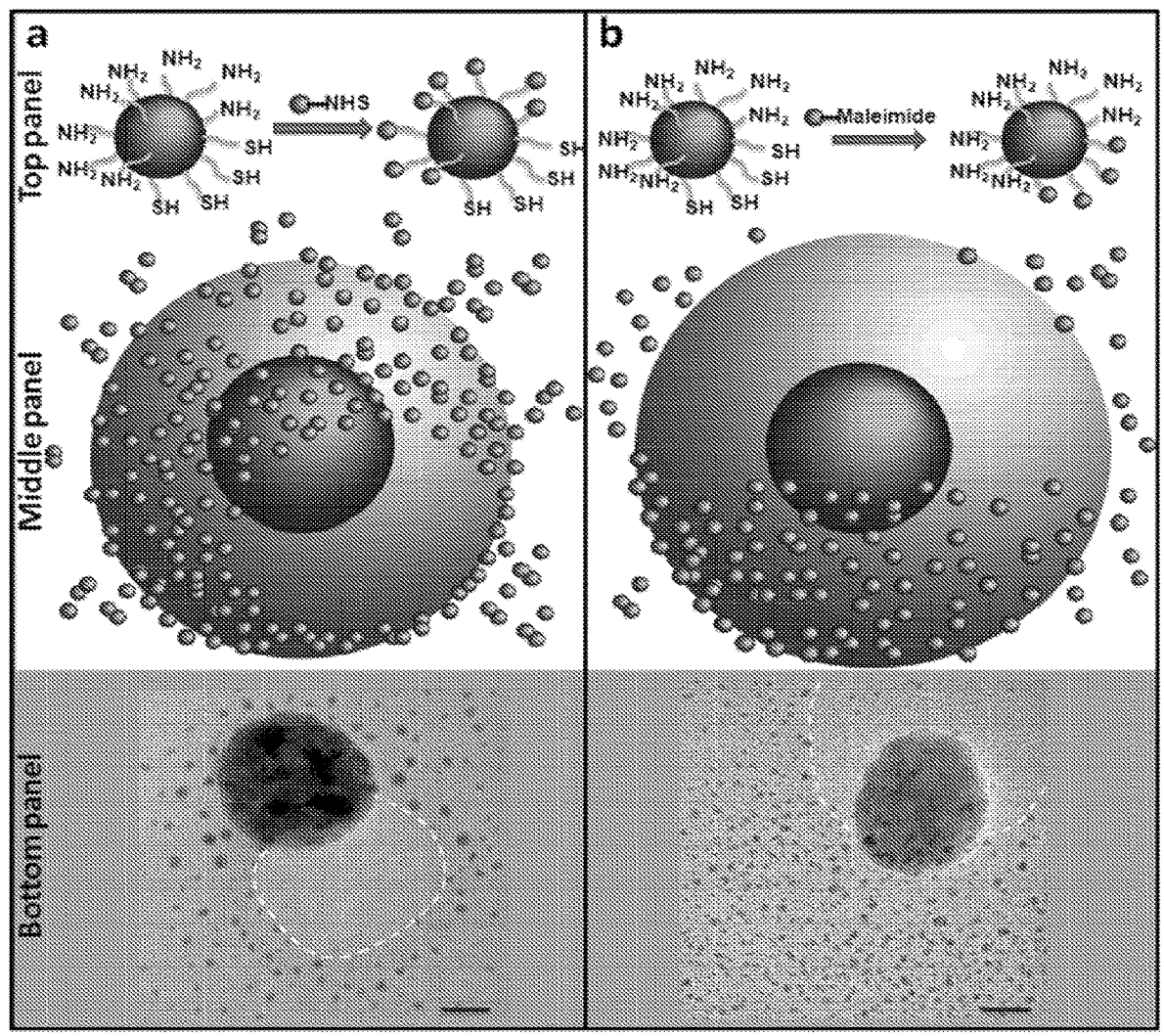
FIGS. 5(a-b) illustrate: (a) TEM image (bottom panel) of an iron oxide nanosphere with an asymmetric surface chemistry displaying a controlled expression of amines and thiols on its surface. Top panel shows an illustration of a 1.4 nm gold probe (AuNP) that was used to tag the amines on the surface of the iron oxide nanosphere using NHS-AuNP. The middle panel shows a cartoon of the iron oxide particle decorated with the AuNP tags. (b) Similarly, maleimide-AuNP was used to decorate the thiols on the surface of the iron oxide particle. Dotted line in yellow indicates the approximate location of the polymer surface with the modified functional group. Scale bar is 10 nm.

The distribution and number of thiols and amines on the nanosphere's surface were evaluated qualitatively using transmission electron microscopy (TEM), theoretically, and quantitatively using fluorescence-based assay. TEM evaluation of the topology of each functional group was achieved by tagging the amines or the thiols on the nanoparticle surface with an excess of the appropriate gold probe (diameter of 1.4 nm) as shown in FIG. 5. More specifically, we incubated the ASC nanospheres (30 nm in diameter) with (a) NHS-functionalized gold probes reactive towards amine groups (FIG. 5a; top panel), (b) maleimide-functionalized gold probes reactive towards thiol groups (FIG. 5b; top panel), (c) non-functionalized gold probes as a negative control (image not shown), and (d) a mixture of NHS- and maleimide-functionalized gold probes as a positive control (image not shown). In the two latter cases, the nanosphere had either no gold probes in its proximity (condition c) or gold probes distributed homogeneously everywhere (condition d). It should be noted that each TEM image is a 2D summation of an iron oxide nanosphere with the iron core being about 30 nm and the polymer coating being about 10 nm as the sketches illustrate (FIGS. 5a and b; middle panel). FIG. 5a (bottom panel) shows that a portion of the nanosphere's surface could not be tagged by the NHS-functionalized gold probe, indicating the absence of amines. In contrast, a smaller portion of the nanosphere's surface could be tagged by the maleimide-functionalized gold probe (FIG. 5b; bottom panel). A visual inspection of the two TEM images implies that about 70% and 30% of the sphere's surface contains amines and thiols, respectively. TEM images of multiple ASC particles have been obtained at different magnifications. We observed that the vast majority of the particles were modified displaying a similar surface asymmetry. However, we elected to display a TEM imaging with one particle at a very high magnification to clearly show the ASC modification.

To study the effect of the nanosphere's diameter and tether length on the surface modification (as shown in FIG. 6a), the partially modified area (PMA) was calculated. The PMA of the nanosphere is defined as the fraction of the surface that is capable to bind to the solid support. Using a combination of Monte Carlo simulations and diffusion reaction theory, we have demonstrated that the binding distance can be approximated as a function of the tether size. For a polymer like polyethylene glycol (PEG), used as a coating of the iron oxide nanosphere, FIG. 6b shows a plot of binding distance as a function of PEG monomers. The binding distance is higher than the equilibrium length of PEG, which is proportional to the Flory radius, and smaller than the maximum extended length of the tether. As shown in FIG. 5c, the PMA is 51.5, 32.1 and 23.6% for a 10, 20 and 30 nm sphere, respectively.

The theoretical design of the ASC nanospheres was validated experimentally using a modification of a previously published fluorescence-based assay. Using Alexa-488-NHS ester to tag the amines on the nanosphere's surface, the fluorescence intensity of the ASC nanospheres was compared to the parent, non-modified nanospheres (only surface amines). The difference in the fluorescence measurements between the ASC and parent spheres is indicated as "modified surface amines" (i.e., amines converted to thiols) in FIG. 6d. These data clearly show the relationship between the size and the surface modification. Since this method takes under account the total number of amine groups on the surface of the nanospheres in the entire suspension, the estimated "modified surface amines" might not be an accurate measure of the modification of each individual particle. However, the fluorescence-based measurement is in fairly good agreement with the theoretical estimation.

Preparation of Linear Nanochains

Figure 7:
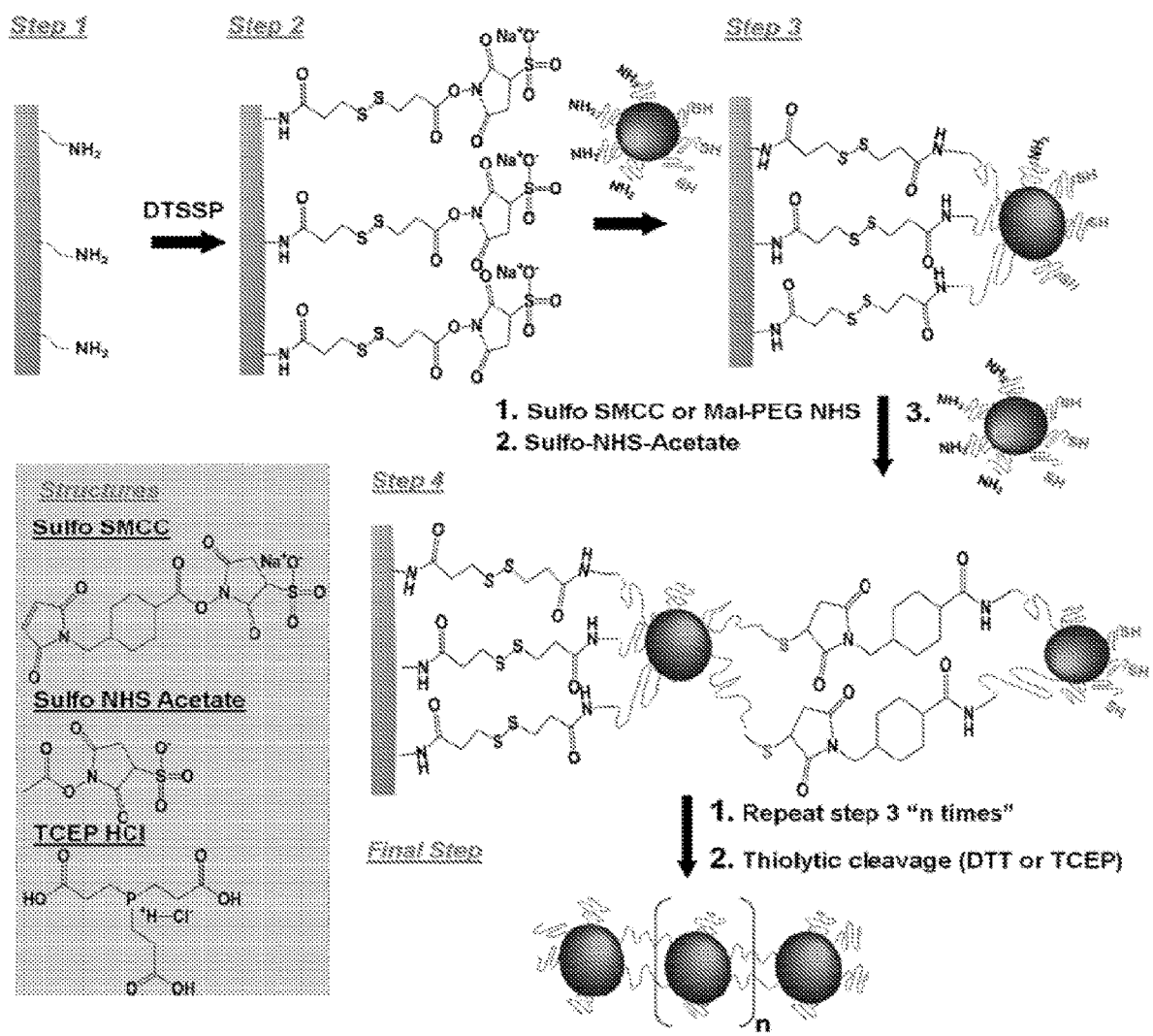
FIG. 7 illustrates a reaction scheme showing controlled assembly of linear nanochains from ASC nanospheres using solid-phase chemistry.

Linear nanochains were assembled from ASC nanospheres on a solid support as shown in FIG. 7. The assembly process began with a solid-phase synthesis similar to the preparation of the ASC nanospheres, using CLEAR resin and DTSSP cross-linker (step 1). The first wave of ASC nanospheres was attached onto the solid support (step 2) followed by an excess of sulfo-NHS acetate to block any unreacted amine groups on the solid phase (step 3). The acetylation/blockage is a crucial step to control the 3D structure of the chain. Step 3 also includes the introduction of the heterobifunctional crosslinker sulfo-SMCC followed by the next wave of ASC nanospheres. This process was continued until the desired length of the nanochain was obtained. A reducing agent, such as DTT or TCEP, was added in the final step to cleave off the final nanochain from the resin.

FTIR analysis was used to monitor the formation of covalent bonds during the synthesis of the nanochains. Following modification of the resin with the crosslinker DTSSP (step 1 in FIG. 7), predominant characteristics of the spectrum included the appearance of IR bands at 525 cm$^{-1}$ (S—S stretching), 1038 cm$^{-1}$ and 1135 cm$^{-1}$ (relatively strong sulfonate resonances), 1790 cm$^{-1}$ and 1730 cm$^{-1}$ (imide resonances), 1650 cm$^{-1}$ (amide I band), 1550 cm$^{-1}$ (week amide II band), and 3040-3700 cm$^{-1}$ (broad region for N—H, O—H stretching from amide and absorbed water). The corresponding bands of the sulfonate (indicative of the NHS ester) and imide groups were used to validate the modification in each step. After step 2 of the synthesis, the IR peaks of the sulfonate and imide groups were significantly reduced in the IR spectrum indicating the attachment of the ASC spheres to the resin. The attachment of the crosslinker sulfo-SMCC to the first ASC sphere (step 3) was confirmed due to the appearance of strong sulfonate peaks and imide bands. As a result of the conjugation of the second ASC sphere onto the nanochains (step 4), the corresponding bands of the sulfonate and imides groups were significantly decreased.

The number and size of the ASC spheres used in the assembly can result in nanochains of different length and aspect ratio. For example, we assembled three different chains consisting of (1) either three consecutive 10 nm spheres (denoted as NC-3×10), or (2) three consecutive 30 nm spheres (denoted as NC-3×30), or (3) two consecutive 30 nm spheres which were sprinkled with 10 nm spheres (denoted as NC-2×30$_{(10)}$). The latter nanochain was created by attaching two spheres of 30 nm on the solid support and conjugating 10 nm spheres onto the available amines on the sides of the chain.

TEM was used to analyze the iron oxide nanochains. As shown in FIG. 6a, NC-3×10 was synthesized in a highly controlled manner. Most of the nanochains are linear and consist of 3 spheres. Notably, all three classes of nanochains displayed a similar consistency. Table 1 summarizes the important parameters of each class of nanochains. In the case of NC-3×10, 3.03 (±0.31) ASC nanospheres per chain were measured via visual inspection of multiple TEM images. Due to the simple and easy removal of unbound spheres in our method, a small number of free nanospheres that were not associated within a nanochain was observed. The hydrodynamic diameter of NC-3×10 was 39.5 nm, whereas the actual size was essentially the summation of the lengths of its constituting spheres. It should be noted that dynamic light scattering measures an effective diameter based on the diffusion of the particle. Similarly, the characteristics of the other two formulations showed a high degree of uniformity indicating the engineerability and great control of the nanochain synthesis.

TABLE 1

Summary of the main characteristics of the three different nanochains

| ID | Hydrodynamic diameter (nm)$^a$ | Nanospheres per nanchain$^b$ | % Nanospheres in nanochains$^c$ |
|---|---|---|---|
| NC-3X10 | 39.5 (±9.1) | 3.03 (±0.31) | 71.3 |
| NC-3X30 | 113.5 (±8.5) | 2.67 (±0.78) | 73.0 |
| NC-2X30$_{(10)}$ | 70.36 (±10.2) | 2.55 (±0.51) | 87.3 |

$^a$Hydrodynamic diameter was obtained from DLS measurements (data presented as mean ± standard deviation).
$^b$Values were obtained from visual analysis of TEM images (minimum count was 200 particles; data presented as mean ± standard deviation).
$^c$The number of nanospheres participating in the formation of nanochains compared to the total number of nanospheres present in the suspension.

To evaluate the effect of the geometry on the magnetization, we compared the r2 relaxivity of the NC-3×30 nanochain to that of its parent 30 nm iron oxide spheres by measuring the transverse (R2) relaxation rates at 1.4 Tesla, a typical field strength used in clinical MRI. Notably, the r2 value of the nanochain is 2.25 times higher than that of its constituting spheres (Table 2).

TABLE 2

Comparison of the T2 relaxivity of a nanochain to its constituting iron oxide nanospheres

| ID | T2 relaxivity (S$^{-1}$ mM$^{-1}$) |
|---|---|
| 30 nm spheres | 44.87 |
| NC-3X30 | 101.05 |

In this example, we were thus able to define the topology of two different functional groups on the surface of a nanosphere using solid-phase chemistry. Based on theoretical and experimental work, the surface asymmetry is partially dictated by the size of the nanoparticle. Importantly, we demonstrated that the surface asymmetry of the nanospheres facilitates the precise assembly of nanochains with well-defined structure. Furthermore, the nanochains exhibited higher magnetic relaxivity than its constituting iron oxide particles.

Example 2

We show in this example that we can integrate the advantages of the molecular and nanoparticle mode of chemotherapeutics into a single agent based on the nanochain technology described in Example 1 and show how this combined mode can be used to significantly improve the outcome of chemotherapy. The nanochain is composed of three iron oxide (IO) nanospheres and one DOX-loaded liposome assembled together in a 100-nm-long chain (abbreviated as DOX-NC). Animal studies indicated that the DOX-NC displayed prolonged blood residence time and enhanced deposition into tumors. Furthermore, animals bearing mammary cancer xenografts showed an improved response, when the DOX-NC treatment was followed by the application of a radiofrequency (RF) field as measured by decreased tumor growth and prolonged survival. We show that the IO tail of the DOX-NC composed of magnetic nanoparticles can serve as a mechanical transducer to transfer RF energy to the liposome membrane. Thus, once DOX-NC has extravasated to the tumor site, RF-induced disruption of the liposomal membrane integrity liberates drug molecules into their free form that can efficiently diffuse into the tumor interstitium (FIG. 9a). This results in a wide-spread anticancer effect as confirmed with histological analysis of apoptosis.

Methods

Synthesis and Characterization of Multi-Component Nanochains

The nanochains were synthesized as described in Example 1. Briefly, solid-phase chemistry was used to partially modify the surface functionality of nanospheres. CLEAR resin (Peptides International Inc, Louisville, Ky.) functionalized with amines was modified with a homobifunctional cleavable cross-linker reactive towards amines (DTSSP). Amine-functionalized IO nanospheres were introduced, allowed to bind to the solid support and then cleaved off using a reducing agent (TCEP). The same type of resin was used and the modified spheres with surface asymmetry were introduced in a step-by-step manner. As a final component, an amine functionalized DOX-loaded liposome was added before recovering the chain via a reducing agent. The chains were characterized in terms of their size (DLS), structure (TEM), and magnetic relaxivity (Bruker minispec relaxometer).

In Vitro RF-Triggered Drug Release

The DOX-NC suspension was exposed to an RF field using a custom-made solenoid (10 kHz frequency at a power of 2-30 Watts into the samples, solenoid's resistance ~5 Ohms). Triggered release from the DOX-NC particles was measured using the fluorescence properties of DOX ($\lambda_{ex/em}$=485/590 nm). The cytotoxicity of released drug from the DOX-NC particles was compared to the liposomal drug and free drug. Briefly, cytotoxicity studies were performed by seeding 13762 MAT BIII cells at a density of $10^5$ cells/well in a 6-well plate 24 h before incubation with the formulations. Prior to incubation, cells were washed three times with fresh medium and then incubated with the treatment for 180 minutes at a concentration of 150 µM doxorubicin per well. The cells were washed three times with fresh medium and incubated for 48 h at 37° C. and 5% $CO_2$ in a humidified environment. The number of viable cells was determined using a formazan-based cell counting assay (CCK-8). Untreated cells were served as live controls for normalization of the data.

Pharmacokinetic Studies

Female Fisher rats were given an IV injection of DOX-NC at a dose of 0.5 mg/kg DOX. Blood was collected from the orbital sinus at various time points before and after injection. Plasma was isolated by centrifugation (2200 g, 15 min), and DOX was extracted after lysis in 30% MeOH and heating at 60° C. for 20 min. The solution was then vortexed and centrifuged. Fluorescent readings of the samples were obtained to detect DOX ($\lambda_{ex}/\lambda_{em}$=485/590) and Alexa-350 on the chain ($\lambda_{ex}/\lambda_{em}$=346/442). Plasma samples obtained immediately prior to injection were used to correct for background fluorescence. Further details are shown in Supporting Information.

Animal Tumor Models

The rat tumor model was established by a subcutaneous injection of $1 \times 10^6$ 13762 MAT B III cells into the right flank of female Fisher rats. Mouse tumors were generated orthotopically in female BALB/c mice by injection of $0.5 \times 10^6$ 4T1 cells into the inguinalmammary fat pad. Once the appropriate tumor size was established (diameter ~0.5 cm), the animals were used in the in vivo studies. Each cell line required different lag times to produce a tumor lesion of about 0.5 cm in size (5 and 8 days for the MAT B III and 4T1 model, respectively). Based on our prior experience, we chose this tumor size as the starting point of the animal studies, since the primary tumor mass is sufficiently large to present angiogenic, necrotic and invasive areas, and therefore may be more informative and relevant to human disease.

Organ Distribution

Twenty four hours after intravenous (IV) injection of the DOX-NC particles or liposomal DOX at a dose of 0.5 mg/kg DOX to the tails of the rat tumor model, the animals were anesthetized and transcardially perfused with heparinized PBS followed by 4% paraformaldehyde in PBS. The organs and tumors were then retrieved, washed with PBS, blotted dry, weighed and DOX was measured following an established protocol.[9] Organ and tumor samples from an animal treated with a saline injection were used to correct for background fluorescence.

Survival Study

Once the appropriate tumor sizes were established (diameter ~0.5 cm), the rat tumor model was IV injected with DOX-NC at a dose of 0.5 mg/kg DOX. After 24 hours from injection, animals were exposed to the RF field operated as described previously. Following the same dose and schedule, control groups included animals treated with DOX-NC (but no RF), only RF, liposomal DOX, liposomal DOX with RF, free DOX, and saline. In addition to the single treatments, another group followed two cycles of treatment. The subsequent treatments were 2 days apart at the same DOX dose followed by exposure to RF following an identical protocol to the first cycle. The tumor growth was monitored every day using caliper measurements. The tumor growth was allowed to progress until the animals showed abnormal symptoms, at which point the animal were euthanized in a $CO_2$ chamber. Time of death was determined to be the following day.

Histological Evaluation

The rat MAT B III and the mouse 4T1 models were used in the histological studies. Animals treated with DOX-NC were exposed to the RF field 24 hours post-injection. After 24 hours from the application of the RF field, the animals were anesthetized with an IP injection of ketamine/xylazine and transcardially perfused with heparinized PBS followed by 4% paraformaldehyde in PBS. Controls included animals treated with DOX-NC (no RF), 35-nm liposomal DOX (with RF), 100-nm liposomal DOX (with RF), free DOX, RF alone and saline. The tumors were explanted and post-fixed overnight in 4% paraformaldehyde in PBS. The fixed tumors were soaked in 30% sucrose (w/v) in PBS at 4° C. for cryosectioning. Serial sections of 12 µm thickness were collected using a cryostat (Leica CM 300).

To visualize the tumor microvasculature, the tissue slices were immunohistochemically stained for the specific endothelial antigen CD31 (BD Biosciences, Pharmingen). The tissues were also stained with the nuclear stain DAPI. To evaluate the spread of the released DOX in relation to location of DOX-NC particles, Prussian blue stain was used to detect iron. Direct fluorescence (red) imaging of tumor sections were performed for imaging DOX. Apoptosis was detected using a TUNEL assay (Promega). The tissue sections were imaged at 20× on the Zeiss Axio Observer Z1 motorized FL inverted microscope. To obtain an image of the entire tumor section, a montage of each section was made using the automated tiling function of the microscope. The total number of cells was counted based on the nuclear stain (DAPI) in multiple histological sections per tumor (minimum 20), whereas apoptotic cells were quantified based on TUNEL-stained nuclei.

Results

Fabrication and Characterization of Multi-Component Nanochains

The nanochain technology is based on a two-step approach to fabricate nanochains using solid-phase chemistry. In the first step, amine-functionalized IO nanospheres were attached on a solid support via a crosslinker containing a disulfide bridge. Liberation of the nanosphere using thiolytic cleavage created thiols on the portion of the particle's surface that interacted with the solid support resulting in a particle with two faces, one displaying only amines and the other only thiols. Therefore, we were able to topologically control the conversion of amines on the surface of the IO nanospheres into thiols, resulting in a particle with asymmetric surface chemistry (ASC). In the second step, employing solid-phase chemistry and step-by-step addition of particles, the two unique faces on the same IO nanosphere served as fittings to assemble them into IO nanochains (FIG. 9b).

The magnetic nanochains were analyzed via visual inspection of multiple TEM images. As shown in FIG. 9c, the magnetic nanochains were synthesized in a highly controlled manner Most of the nanochains are linear and consist of 3 IO spheres. To evaluate the robustness of the nanochain synthesis, the number of IO nanospheres per nanochain was measured in multiple TEM images (minimum count was 200 particles). While 16% of the total particles in the suspension were the parent (unbound) IO spheres, the majority of the particles (73%) comprised of nanochains with 3 IO spheres (8 and 4% were nanochains with 2 or 4 IO spheres, respectively). Importantly, our methodology offers exceptional flexibility in synthesizing nanochains consisting of various types of constituent members with different functions. Specifically, in the last step of synthesis, we attached one drug-loaded liposome per magnetic nanochain (FIG. 9d). The final nanoparticle consisted of three IO spheres and one DOX-loaded liposome with the overall geometrical dimensions of the DOX-NC particle being about 100×30 nm (length×width), which was essentially the summation of the lengths of its constituent IO spheres and liposome. A design criterion was to use a liposome with a size that is comparable to that of the IO spheres of the magnetic nanochain. We therefore used DOX-loaded liposomes with a hydrodynamic diameter of about 30 nm, which were fabricated using a combination of extrusion and sonication. As shown in FIG. 9e, the hydrodynamic size of the final DOX-NC particle and each component separately, as measured by dynamic light scattering (DLS), verified the TEM findings. It should be noted that DLS measured the effective hydrodynamic diameter based on the diffusion of the particles. Due to the high intraliposomal space available for drug encapsulation and the efficient remote loading technique, the DOX cargo of DOX-NC was high (i.e. $6.8 \times 10^{-5}$ ng/DOX-NC particle).

In Vitro On-Command Triggered Drug Release Using RF

Through their interaction with magnetic fields, the magnetic component (JO spheres) of the DOX-NC particle efficiently converts magnetic energy to mechanical energy, which is dependent on the strength and frequency of the magnetic field, as well as the configuration of the IO spheres in the nanochain. Thus, drug release can be remotely triggered due to defects of the liposomal membrane caused by the oscillation of the magnetic 'tail' of the DOX-NC particle in the presence of an RF field (FIG. 10a). Magnetic field generation was accomplished using an RF source and a solenoidal coil that was size-matched to the sample, which was placed inside the coil. FIG. 10b shows that the release of DOX can be triggered in a controlled manner under the RF field (10 kHz frequency, 1-50 W dissipated power) at a very low concentration of DOX-NC particles expected to deposit in tumor tissues during in vivo applications. Notably, the release rate could be modulated by adjusting the operating parameters of the RF field. We should emphasize that no temperature increase occurred in the DOX-NC suspension under the 'mild' RF field (experiment was performed at room temperature).

The DOX release profile from DOX-NC particles in the absence of RF is shown in FIG. 10c. To investigate the effect of temperature on the release rate, the DOX-NC suspension was incubated at different temperatures for 60 min. A 5% release of the DOX cargo was released at 37° C., which is consistent with the behavior of the parent liposome. The liposome component of the DOX-NC particle is composed of the phospholipid DPPC, which does not result in thermosensitive liposomes. While DPPC membranes have a transition temperature of 41° C., the addition of cholesterol to the liposomal membrane has a significant stabilizing effect. Due to the increased transition temperature of the DPPC/cholesterol membrane ($T_m$>50° C.) and the stable entrapment of the precipitated DOX in the liposome, a minor increase in release of DOX is expected at elevated temperature due to increase of DOX solubility. Thus, the time course of the release profiles showed an initial burst in the first 5 min followed by a plateau (data not shown). A temperature of 50° C. was required to cause a significant release in 60 min, which is significantly higher than the observed temperature of the release experiment under the RF field.

To further investigate whether mechanical vibration is the release mechanism, we measured the release from suspensions of dramatically different concentrations of DOX-NC under the same RF field. As shown in FIG. 10d, the same release rate per DOX-NC particle is achieved from low concentrations as well as very high concentration of the particles. So far the in vitro studies excluded bulk heating of the DOX-NC suspensions under the RF field. However, significant local heating can be generated around nanoparticles. To explore the possibility of local heating, a fluorophore linked on the surface of the DOX-NC particle was used as a thermometer based on an established method. There is no significant heat generation around the DOX-NC particles. Thus, contrary to heat-induced drug release, we can conclude that the triggered release mechanism of DOX-NC is concentration-independent and is probably based on mechanical forces that occur on the single particle scale. We then investigated the dependence of the release rate on the distance of the DOX-NC suspension from the RF source. FIG. 10e shows that the release rate is significantly lower at 4 cm away from the RF coil after a 90 min exposure (P<0.01), which is consistent with the relationship of the magnetic field strength to distance (FIG. 10f). Furthermore, FIG. 10g shows the cytotoxic effect on mammary adenocarcinoma cells (13762 MAT BIII) of released DOX from DOX-NC, non-released DOX-NC, empty nanochains (no DOX), and free DOX. The empty nanochain had no effect on cancer cells. While DOX-NC had moderate cytotoxicity, the RF-triggered release of DOX from DOX-NC had significantly higher cytotoxic effects (P<0.01) due to release of free DOX. Notably, the released drug is 100% bioavailable.

Blood Circulation and Tumor Deposition of Nanochains

Plasma clearance studies were performed on animals without tumors in order to evaluate only the effects of phagocytic clearance. Following an intravenous injection of DOX-NC at a dose of 0.5 mg DOX per kg body weight, FIG. 11a shows that the 100-nm-long DOX-NC particle exhibited prolonged blood residence time (blood $t_{1/2}$~26 hours). For comparisons, we used a long-circulating 100-nm liposome (blood $t_{1/2}$~18 hours) due to its long and successful history of encapsulating DOX for clinical use. In addition, the concentration profiles of DOX-NC in the blood measuring either the DOX levels (liposome component) or the fluorescently tagged IO spheres (IO tail component) matched suggesting that the structure of the DOX-NC particle remains intact during circulation in blood.

Using a dose of 0.5 mg/kg DOX, we evaluated the organ and tumor distribution of DOX-NC in the 13762 MAT B III tumor model, which is a rat-syngenic aggressive mammary adenocarcinoma. The animals were euthanized 24 hours after intravenous administration of DOX-NC or 100-nm liposomes, and the organs and tumors were extracted and analyzed for DOX content. The accumulation of DOX-NC in the heart, lungs and kidney was about 5% or less of the injected dose (FIG. 11b), which was comparable to the behavior of the 100-nm liposomes. More importantly, the uptake of DOX-NC by the liver was significantly lower than that of liposomes (P<0.01). Taking under consideration that nanoparticles are primarily cleared by the reticuloendothelial system, the low uptake of DOX-NC by the liver correlates to its prolonged blood residence. DOX-NC outperformed the 100-nm liposomes as indicated by their higher intratumoral accumulation (FIG. 11b, P<0.01). This is likely due to the fact that nanoparticle extravasation into tumors is directly proportional to their blood residence time.

Therapeutic Effectiveness in a Rat Breast Tumor Model

The MAT B III tumor-bearing animals were intravenously injected with DOX-NC at a low dose (0.5 mg DOX per kg body weight). Typical dosage of liposomal DOX is 10-20 times higher and ranges from 5-10 mg/kg in animal studies. Since a significant amount of DOX-NC is deposited into tumors by 24 hours after injection, the RF field was utilized at this time point. As shown in FIG. 12a, 24 hours after injection, the RF field (10 kHz/3-5 W) was applied for 60 min using the RF coil positioned 1 cm from the animal and oriented such that the magnetic field was directed toward the tumor. Iron staining of histological sections using Prussian blue showed that DOX-NC particles were well-distributed within the tumor interstitium at 24 hours post-injection (FIG. 12b). In contrast, no Prussian blue staining was observed in tumors treated with liposomal DOX (images not shown). Without the application of RF, direct fluorescence (red) imaging of the histological sections failed to detect free DOX (images not shown). Hence, the drug is still incorporated into the nanochain with the fluorescence signal of intra-liposomal DOX being quenched. Following the application of the RF field, free DOX was widely spread in the tumor extravascular space and localized in the nuclei of the tumor cells (FIG. 12c).

After we recognized that DOX-NC can efficiently deposit into tumors, the tumor response to DOX-NC was evaluated by quantitatively following the tumor size for several days after injection. Based on the fact that DOX-NC displayed significant accumulation in the tumor at 24 hours post-injection, the application of the RF field 24 hours after injection of DOX-NC significantly suppressed tumor growth as shown in FIG. 12d (P<0.01). As expected, application of the RF alone had no effect on the tumor growth rate. Animals treated with the same low dose of DOX of clinically used free DOX, 35-nm or 100-nm liposomal DOX followed by RF failed to produce any therapeutic benefits. While a single treatment of liposomal DOX has generated therapeutic benefits in animal tumor models, the administrated dose was 10-20 times higher than the dose we used. Even though DOX-NC achieves higher accumulation in the tumor than the 100-nm liposomal DOX (as shown in FIG. 11b), there was no substantial effect on the tumor growth rate (without the application of RF). In conjunction to the slow release of DOX from DOX-NC, we speculate that this is related to the very low dose of DOX. Based on the same dose per treatment, we also employed a two-cycle treatment using DOX-NC (at days 5 and 7 after tumor inoculation) followed by RF application (at days 6 and 8). As shown in FIG. 12d, the multiple treatments accomplished greater tumor shrinkage than a single treatment.

Furthermore, the therapeutic efficacy of the DOX-NC treatment followed by RF was determined by comparing the survival times of treated animals to untreated animals. The group treated with DOX-NC followed by RF exhibited a statistically significant increase in survival time (25.1±3.8 days) compared to the untreated group and the other groups that received single treatment (survival ~15.2±2.4 days). Notably, the two-cycle treatment using DOX-NC followed by RF prolonged the survival to a greater extent than the single treatment (46±8.1 days). These in vivo studies using systemic administration of DOX-NC at a dose of 0.5 mg/kg DOX demonstrate that 1) nanochains effectively extravasate into tumors and 2) RF application to DOX-NC-treated tumors enhanced the therapeutic outcome.

Histological Evaluation of the Anticancer Efficacy

In addition to the improved therapeutic outcome as measured by lower tumor growth and prolonged survival, we sought to verify that the anticancer activity of DOX-NC is based on improved distribution of free drug after application of the RF field. Since DOX is a weak fluorophore, direct fluorescence imaging of DOX provided a qualitative demonstration of the RF-triggered drug release. We then performed histological analysis of apoptosis using the more sensitive TUNEL assay to quantitatively evaluate the extent and topology of the apoptotic cells in response to DOX-NC. It should be noted that dark color indicates apoptotic cells in FIG. 13 and not molecules of DOX. Following a single injection of a DOX treatment, animals were euthanized 24 hours post-injection and tumors were excised. Visual inspection of histological images of tumors treated with free DOX at the regular dose (i.e. 5 mg/kg) showed a substantial number of apoptotic cells (FIG. 13a). Tumors treated with 100-nm liposomes (FIG. 11b) or DOX-NC (FIG. 13c) at the low dose of 0.5 mg/kg DOX displayed a small number of apoptotic cells primarily in the well-vascularized rim. Importantly, negligible apoptosis was observed after systemic administration of empty nanochains (no DOX cargo) followed by RF (FIG. 13d), suggesting that limited or no RF heating of the magnetic nanospheres takes place. However, RF application on DOX-NC-treated animals resulted in massive apoptosis in both the well-vascularized rim and the less vascularized inner core (FIG. 13e).

To obtain a quantitative evaluation, the total number of cells was counted based on the nuclear stain (DAPI) in multiple histological sections (minimum 20) per tumor, whereas apoptotic cells were quantified based on TUNEL-stained nuclei. The percent of apoptotic cells relative to the total number of cancer cells was used as a measure of the anticancer efficacy. Using the CD31 staining of the microvasculature, we drew ROIs to distinguish apoptosis in the rim from the core of the tumor. FIG. 14a shows that 2.3 and 13.8% of the cancer cells were apoptotic in the case of tumors treated with the 100-nm liposome and DOX-NC, respectively. In good agreement with the previous in vivo studies (e.g. tumor distribution and survival), DOX-NC exhibited greater cytotoxicity than the 100-nm liposomes. As expected for both the liposomes and DOX-NC, the anticancer effect was more profound in the rim of the tumors, where about 8 times more apoptotic cells were observed compared to the less vascularized core (FIG. 14b). On the other hand, the combination of DOX-NC and RF resulted in 34.2% of the cancer cells being apoptotic, which was a significant increase of apoptosis compared to any other treatment (P<0.01). This is also in good agreement with our previous observation that released DOX was found in the cancer cell nuclei. In fact, previous studies have shown that nuclear DNA functions as a sink for DOX. More importantly, the apoptotic results were equally elevated in the core and the rim of the tumors. Application of RF on DOX-NC-treated tumors exhibited 5 and 18 times greater apoptosis in the core of tumors compared to DOX-NC (no RF) and liposomes (with RF), respectively. Taking under consideration this rat breast tumor model is highly aggressive, having a core with little or no vascularization, the apoptotic index indicates that RF liberates bioavailable drug into non-vascularized regions resulting in a wide-spread anticancer effect throughout the entire tumor.

Since the intratumoral penetration of therapeutic molecules and nanoparticles is highly variable between different types of cancer and different species, we tested DOX-NC in an orthotopic 4T1 mammary tumor model in mice. As shown in FIGS. 15a and b, tumors treated with the 35-nm liposomal DOX exhibited more apoptotic cells than the 100-nm liposomal DOX. Similarly to the MAT B III model, the 4T1 tumors treated with DOX-NC (FIG. 15c) displayed higher levels of apoptosis than both liposomal treatments. As shown in FIG. 15d, tumors treated with DOX-NC followed by RF substantially increased the number of apoptotic cells. FIG. 15e summarizes the quantification of the apoptotic index of the various treatments, which is highly consistent with the data obtained from the MAT B III model. For example, the percent of apoptotic cells was elevated about 2 fold in tumors treated with the combination of DOX-NC and RF (37% apoptotic cells in the tumor mass; P<0.01) compared to DOX-NC without RF (20%). We should note the 4T1 tumors do not present a clear hypervascularized rim and a less vascularized/avascular core resulting in a more consistent rate of apoptosis throughout the tumor.

The histological studies evaluated the anticancer efficacy of DOX-NC using a single administration of the agent at a low dose of 0.5 mg/kg DOX. Overall, the apoptotic index in both animal models indicates that the RF-triggered release from DOX-NC substantially improved the interstitial transport and spatial distribution of the drug compared to the control treatments.

In this example, we thus demonstrated that a nanochain-based chemotherapeutic enabled the delivery of the cytotoxic drug, doxorubicin to the majority of cancer cells throughout a tumor. Successful drug delivery to tumors requires that a long-circulating nanoparticle 1) enters the tumor microcirculation, 2) navigates through the tumor leaky vasculature into the tumor interstitium, and 3) releases the drug close to cancer cells. The nanoparticle system shown here meets all of these requirements. Due to their prolonged blood circulation, the nanochains capitalized on the EPR effect, and showed a high concentration in the tumor. Furthermore, once these multi-component nanoparticles extravasated into the tumor site, RF-triggered drug release resulted in a wide-spread cytotoxic effect throughout the entire tumor. Taking under consideration that RF can penetrate deep into tissues, this platform technology will effectively deliver drugs to primary and metastatic tumors with all the benefits of reduced side effects and substantial impact on cancer treatment.

Example 3

In this example, we describe the design of a nanoparticle targeting $\alpha_v\beta_3$ integrin for non-invasive imaging of metastasis (FIG. 16a). Specifically, we selected the cyclic tripeptide arginine-glycine-aspartic acid (cRGD) peptide as the ligand for vascular targeting of the nanoparticle to metastases. We exploited the nanochain technology described in Example 1 to fabricate a chain-shaped nanoparticle composed of four iron oxide (IO) nanospheres chemically linked into a linear assembly (FIG. 16b). The high aspect ratio and flexibility of the nanoparticle substantially increased its chances to successfully seek metastatic lesions due to geometrically enhanced multivalent docking to the vasculature of metastases. Due to this high avidity and increased magnetic relaxivity of the nanochain particles, we were able to detect metastatic lesions in an aggressive breast tumor model in mice using small animal fluorescence molecular tomography (FMT) and magnetic resonance imaging (MRI). This approach is useful for selective targeting of therapeutic agents to metastases.

Methods

Synthesis and Characterization of the Nanochain Particles

The nanochains were synthesized as described in Example 1. Briefly, solid-phase chemistry was used to partially modify the surface functionality of IO nanospheres. CLEAR resin (Peptides International Inc, Louisville, Ky.) functionalized with amines was modified with a homobifunctional cleavable cross-linker reactive towards amines (DTSSP). Amine-functionalized IO nanospheres were introduced, allowed to bind to the solid support and then cleaved off using a reducing agent (TCEP). The same type of resin was used and the modified spheres with surface asymmetry were introduced in a step-by-step manner. After recovering the chain via a reducing agent, the suspension was further cleaned using dialysis. The nanoparticles were characterized in terms of their size (DLS), structure (TEM), and magnetic relaxivity (Bruker minispec relaxometer). The cyclo (Arg-Gly-Asp-D-Phe-Cys) or c(RGDfC) was conjugated onto PEG(3400) via maleimide chemistry. In addition to conjugation of the cRGDe peptide, the nanochain particles were tagged with an NIR fluorophore (Vivotag 680) to be detectable by FMT imaging or fluorescence spectroscopy or microscopy. Details of the synthesis and characterization of the nanoparticles are shown in the Supporting Information.

Mouse Tumor Model

We used an orthotopic 4T1 breast tumor model in mice. The 4T1 cell line was engineered to stable express green fluorescent protein (GFP) to allow tracking and quantification of the cells in vivo and histologically. Briefly, we inoculated $0.5 \times 10^6$ 4 T1 cells orthotopically in a no. 9 mammary fat pad of female BALB/c mice that was surgically exposed while the mice were anesthetized. The animals were used in the in vivo studies at week 2 (only primary tumor) or week 5 (primary and metastatic tumors). Based on our prior experience, we chose these time points, since they represent different stages of angiogenesis, necrosis, invasion, and metastasis and are informative and relevant to the human disease.

Fluorescence Molecular Tomography

We performed fluorescence imaging on the 4T1 mammary model in mice (at week 2 or 5) using the FMT 2500 Quantitative Tomography In Vivo Imaging System (Perkin Elmer). Phantoms for each nanoparticle formulation were used to calibrate the FMT to take quantitative deposition measurements. We then intravenously injected each of the four formulations at a dose of $1.3 \times 10^{14}$ particles per kg b.w. The animals were imaged before and after IV injection of the formulations at multiple time points (15, 30, 45 min and 3, 6, 24 h). After the last imaging session, tumor and organs (kidneys, lungs, brain, liver, spleen and intestine) were retrieved and weighed. To verify the findings of the in vivo imaging and confirm the presence of metastases in the organs, we imaged the organs ex vivo using the FMT and a CRi Maestro fluorescence imaging system. The organs were then processed for histological analysis.

Angiography Using Contrast-Enhanced Micro-CT Imaging

Contrast-enhanced angiography was performed using a Siemens Inveon micro-CT system (isotropic 99 μm resolution, 80 kVp, 500 μA) and a long-circulating liposomal imaging agent encapsulating a high cargo of an iodinated contrast agent. Following IV injection of the agent at a dose of 2.6 g iodine/kg b.w., the animals were imaged with the micro-CT system. Subsequently the animals were IV injected with RGD-NC followed by imaging with the FMT system. The two images were co-registered using a semi-automatic 3D segmentation-based registration approach that was implemented in script-based software (in MATLAB) and interactive visualization software Amira (Visage Imaging Inc). Fiducial markers placed around the tumor mass were visible in both the micro-CT and the FMT images. Using a region growing algorithm with seed points defined by the user, we segmented the fiducial markers from both volumes. Then, we used Amira's AffineTransform tool to register the floating volume landmarks to the reference volume landmarks.

MRI Imaging

MRI images were acquired on a 9.4 T Bruker MRI system. A volume coil (3.5-cm inner diameter) was employed. High resolution images were obtained before and 15, 30, 45, 60 and 120 min after IV injection of the RGD-NC nanoparticles (at a dose of 7.5 mg Fe/kg b.w.) using a T2-weighted RARE sequence with the following parameters: TR/TE=1000/45 msec, matrix=128×128, FOV=5×5 cm, and 1 average. This resulted in an in-plane spatial resolution of 390 μm and a slice thickness of 1 mm Histological Evaluation After the last imaging acquisition with FMT or MRI, tissues were collected from the mice for histological studies. The animals were anesthetized with an IP injection of ketamine/xylazine and transcardially perfused with heparinized PBS followed by 4% paraformaldehyde in PBS. Tumors and organs were explanted and post-fixed overnight in 4% paraformaldehyde in PBS. The tissues were soaked in 30% sucrose (w/v) in PBS at 4° C. for cryosectioning. Serial sections of 12 μm thickness were collected using a cryostat (Leica CM 300). To visualize the tumor microvasculature, the tissue slices were immunohistochemically stained for the endothelial antigen CD31 (BD Biosciences, Pharmingen). The tissues were also stained with the nuclear stain DAPI. Standard hematoxylin-eosin staining was also performed. The tissue sections were imaged at 5, 10 or 40× on the Zeiss Axio Observer Z1 motorized FL inverted microscope. To obtain an image of the entire tissue section, a montage of each section was made using the automated tiling function of the microscope.

Results

Fabrication and Characterization of the Integrin-Targeted Nanoparticle

Fabrication of the integrin-targeted nanoparticle (termed RGD-NC) was based on the nanochain technology, which is a two-step approach using solid-phase chemistry. In the first step, amine-functionalized IO nanospheres were attached on a solid support via a crosslinker containing a disulfide bridge. Liberation of the nanosphere using thiolytic cleavage created thiols on the portion of the particle's surface that interacted with the solid support resulting in a particle with two faces, one displaying only amines and the other only thiols. Therefore, we were able to topologically control the conversion of amines on the surface of the IO nanospheres into thiols, resulting in a particle with asymmetric surface chemistry. In the second step, employing solid-phase chemistry and step-by-step addition of particles, the two unique faces on the same IO nanosphere served as fittings to assemble them into linear nanochains (FIG. 16b). The nanochains were analyzed via visual inspection of multiple TEM images. As shown in FIG. 16c, the nanochains were synthesized in a highly controlled manner Most of the nanochains are linear and consist of 4 IO spheres with the overall geometrical dimensions of the particle being about 100×20 nm (length×width). To evaluate the robustness of the nanochain synthesis, the number of IO nanospheres per nanochain was measured in TEM images. While 6% of the total particles in the suspension were the parent (unbound) IO spheres, the majority of the particles (72%) comprised of nanochains with 4 IO spheres (12 and 10% were nanochains with 3 or 5 IO spheres, respectively). As shown in FIG. 14d, the hydrodynamic size of the particle and its constituent IO spheres, as measured by dynamic light scattering (DLS), verified the TEM images. It should be noted that DLS measured the effective hydrodynamic diameter based on the diffusion of the particles. Since the hydrodynamic diameter measured by DLS does not correspond to the geometrical size of non-spherical particles, we relied on visual analysis of TEM images to measure the exact dimensions of the nanochain. Detailed characterization of the nanochain particles is reported in a previous publication.

The cyclo (Arg-Gly-Asp-Phe-Cys) or c(RGDFC) (SEQ ID NO: 2) was conjugated onto the distal end of the PEG-NH$_2$ on the particle's surface. While FIG. 16c shows the nanochain after modification with the RGD peptide. In addition to conjugation of the peptide, the nanochain particles were labeled with an NIR fluorophore (VivoTag 680) to be detectable by fluorescence imaging. To evaluate the effect of the geometry on the magnetization, we compared the r2 relaxivity of the RGD-NC particle to that of its parent IO nanospheres by measuring the transverse (R2) relaxation rates at 1.4 Tesla. The r2 value of the RGD-NC particle was 121 s$^{-1}$ mM$^{-1}$, which was 2.1-fold higher than that of its constituent IO spheres. Detection of metastasis via receptor-mediated targeting depends on the generation of signal from each nanoparticle. Thus, we calculated the T2 relaxivity on a per nanoparticle basis, which was 8.4 times higher for the RGD-NC particle compared to its constituent IO nanospheres.

Targeting of the RGD-NC nanoparticles to integrin-expressing endothelial cells was evaluated in vitro under static and flow conditions. Bovine aortic endothelial cells (BAEC) were treated with TNF-$\alpha$ to induce expression of $\alpha_v\beta_3$ integrins and then incubated with an excess of the RGD-NC nanoparticles for different periods of time. As shown in Figure S2a in Supporting Information, the time course of the nanoparticle uptake by the cells showed that the binding of the nanoparticles occurs rapidly during the first 30 min of incubation. In a similar manner, we evaluated the cellular uptake by 4T1 cells indicating that the integrin-targeting RGD-NC nanoparticles were also able to target the cancer cells (Figure S2b). This is significant, because the metastatic 4T1 cells colonize the endothelium as we show later in the histological evaluation.

Successful vascular targeting requires that a nanoparticle can escape the blood flow and drift towards the blood vessel walls (e.g. high margination), followed by strong attachment to the targeting site offsetting the blood flow forces that tend to detach the particle (e.g. high avidity). Since both margination and avidity of nanoparticles in circulation strongly depends on the geometry of the nanoparticle, we measured the margination rates and avidity of the nanochains in microvasculature constructs under flow conditions using our previously established in vitro method. The experiments were conducted in a microfluidic flow network setup, because channel dimensions and infusion rates can be accurately controlled removing the complexity of in vivo studies. Firstly, TEM images of the nanochain suspension in cell culture media were obtained, after the nanoparticles were flowed in the microchannel for 20 min at 50 µL/min, indicating that the particles maintain their structural integrity under flow conditions. To separate margination from targeting avidity, we initially evaluated the margination of non-targeted nanochains. To avoid undesirable specific binding events, the channel was coated with fibronectin, which captures marginating particles in a broad non-specific manner. At a flow rate of 50 µL/min, which is in the range of expected blood flow in tumor microcirculation, the nanochain exhibited 2.3-fold higher margination than the IO sphere. Targeting avidity of the RGD-NC particle was also assessed under flow using the microfluidic device coated with TNF-$\alpha$-treated BAEC cells. RGD-NC nanoparticles and RGD-targeted nanospheres displayed a biphasic behavior comprising of an initial rapid attachment phase followed by a slower attachment rate. Importantly, after 5 and 20 min, the RGD-NC nanoparticles achieved 9.5 and 2.9-fold higher attachment compared to their spherical counterparts. We should note that the ligand density on the surface of nanospheres or nanochains was the same being about 25 RGD peptides per sphere. Thus, the total number of RGD peptides on a nanochain was about 100.

Targeting the Primary Tumor

We used the orthotopic 4T1 mammary tumor model in mice to assess the potential utility of RGD-NC nanoparticles for detection of primary tumors and metastases. The 4T1 cell line is one of the few breast cancer models that efficiently metastasizes to sites and organs similar to that observed in the human disease. Previous studies have shown that growth of cells at the primary site displays a biphasic behavior: 1) the primary tumor rapidly grows in the first 2 weeks after inoculation of tumor cells in the mammary fat pad; 2) the tumor shrinks in the next 2 weeks due to infiltration of leukocytes and extensive necrosis; 3) during the 5th week, the tumor grows again with metastases occurring primarily in the liver, spleen and lungs.

Initially, we compared the RGD-NC particles to RGD-targeted IO nanospheres (RGD-NS) and their non-targeted variants in their ability to target the primary tumor (early-stage: week 2 after tumor inoculation). All formulations were administered at a dose containing an equal number of particles per kg of body weight (i.e. 1.3×10$^{14}$ particles/kg b.w. corresponding to 0.21 and 0.87 mg Fe/kg b.w. for the IO nanospheres and nanochains, respectively). Using Fluorescence Molecular Tomography (FMT) imaging, we non-invasively and quantitatively monitored the time-dependent intratumoral accumulation of the various particles (equal number of NIR fluorophores/particle). FIG. 17a shows representative FMT images that were taken 30 min after systemic administration of the formulations. Due to their enhanced multivalent docking, the RGD-NC nanoparticles substantially outperformed the targeted nanospheres. As expected, the non-targeted nanochains exhibited slow accumulation into the primary tumor primarily due to the EPR effect. As shown in FIG. 17b, the intratumoral accumulation of the non-targeted nanochains was about 5.9% of the injected dose at t=3 hours post-injection. We should emphasize that the nanochains and nanospheres were not fully covered with the polyethylene glycol (PEG) coating. This is evident by the blood residence time of the nanoparticles shown in FIG. 17c (blood $t_{1/2}$~20 min; measured in the heart), since the circulation time of nanoparticles depends on the degree of PEG shielding. Our objective was to detect signal from the RGD-NC particles targeting integrins on the tumor-associated vascular bed with no interference from signal in the vascular site. If the particles are bound to the tumor vasculature, the time point of maximum signal from the tumor site should coincide with low concentration of the nanoparticles in the bloodstream. FIG. 17d shows the time course of the fluorescent signal in the tumor for each formulation. Indeed, the RGD-NC-injected animals displayed maximum signal in the tumor in the 30-60 min time window, while the nanoparticles were almost depleted from the bloodstream. Most importantly, at t=45 min after injection, the tumor accumulation of RGD-NC was 8-fold higher than their non-targeted variant. At that time point, vascular targeting via the RGD peptide resulted in more than 40% of the administered nanochains being localized in the primary tumor. Quantitative measures of the intratumoral deposition of each particle (i.e. area under the curve and maximum signal denoted as AUC$^{0 \to 1h}$ and signal$_{max}$, respectively) are shown in the table of FIG. 17d. In general, these data are consistent with the in vitro targeting experiments showing that the RGD-NC particles achieved significantly higher vascular targeting at an earlier time point. At later time points, low levels of agent remained in circulation 24 hours after administration. Mostly the agent was found in the liver and spleen with less that 5% of the injected dose being in the heart, kidney.

To validate the in vivo FMT-based measurements, the iron concentration of the primary tumors of animals injected with the formulations was directly measured ex vivo using ICP-OES (inductively coupled plasma optical emission spectroscopy). Animals injected with saline were used for correction of the background levels of iron in the tumor tissue. FIG. 17e shows the intratumoral iron content 30 min after injection of targeted and non-targeted nanochains and nanospheres, verifying the patterns observed with FMT imaging. While the FMT measurements slightly overestimated the intratumoral concentration of the nanoparticles compared to the ICP measurement, the only statistically different condition was the case of RGD-NS. Notably, ICP confirmed that more than 35% of the administered RGD-NC particle accumulated in the tumor within 30 min after administration.

Targeting Metastases

To evaluate the ability of the RGD-NC particles to target metastasis, we used mice with a late stage 4T1 tumor (week 5 after tumor inoculation). We performed whole body angiography at 99 µm resolution using a micro-CT system (Siemens Inveon) and a liposomal imaging agent encapsulating a high cargo of an iodinated contrast agent. Consistent with previous reports, FIG. 18a indicates that the primary tumor of this animal model at a late-stage presented a necrotic core with little internal vascularization and a vascularized periphery. The same animal was systemically injected with RGD-NC nanoparticles tagged with an NIR fluorophore and imaged with the FMT system. 3D-rendered volumes of the micro-CT angiogram and the FMT image (45 min post-injection) were co-registered using a script-based software (in MATLAB) and the interactive visualization software Amira (FIG. 17b). The accumulation of the RGD-NC particles in the primary tumor site was primarily observed in the location of blood vessels, which is consistent with the expression of integrins due to tumor-associated angiogenesis. Importantly, significant fluorescence signal was detected in other organs away from the primary tumor site. Based on previously published work, regions of interest (ROIs) were selected in the FMT image to indicate the location of major organs (FIG. 18c), showing that the RGD-NC nanoparticles accumulated in other organs besides the primary tumor (e.g., liver and lungs). To confirm the colocalization of RGD-NC particles and metastatic tumors, organs were imaged ex vivo using a CRi Maestro fluorescence imaging system, since the 4T1 cell line was engineered to stably express green fluorescence protein (GFP). We should note that the fluorescence signals from GFP and the nanoparticle's NIR tag do not overlap. FIG. 18d confirms the presence of metastatic tumors in the liver, spleen and lungs (other organs are not shown, since no signal from GFP was detected). Grossly, the metastatic tumors appeared as white nodules in bright field imaging, compared to the darker liver parenchyma. More importantly, the signals from metastatic cancer cells and RGD-NC particles overlaid significantly indicating the localization of the nanoparticles in metastatic lesions.

The efficacy of the RGD-NC nanoparticles to target metastatic tumors was quantitatively evaluated in a group of mice harboring metastatic 4T1 tumors (n=6) using FMT imaging. FIG. 19a shows representative images of a normal mouse (top row) and a mouse with metastases (bottom row) imaged with the FMT system at t=30 min after injection of RGD-NC. The relatively low signal in the lungs of normal animals (n=6) suggested the presence of the agent primarily in the bloodstream. Since RGD-NC nanoparticles are primarily cleared by liver Kupffer cells (and splenic macrophages), the liver of the same animals exhibited relatively appreciable signal compared to the lungs. On the other hand, FMT imaging of mice with late stage 4T1 tumors showed significant accumulation of RGD-NC primarily in regions of the liver and lungs. Using the designated ROIs for each organ (as shown in FIG. 18c), we measured the concentration of RGD-NC in locations of those organs displaying significantly enhanced signal (i.e. hot spots). In each 'metastatic' animal, we identified 1-3 hot spots in the liver and lungs designated as ROI-1 and ROI-2 in FIG. 19a, respectively. The quantitative analysis shown in FIG. 19b revealed a significant concentration of the agent in these hot spots. More importantly, these hot spots displayed a 15 and 7.2-fold increase of signal compared to the background signal in healthy liver and lungs.

Imaging of Metastasis Using MRI

To detect metastases using a clinically relevant imaging modality, we performed imaging with MRI. FIG. 20 shows representative coronal T2-weighted images of healthy mice (n=3) and metastatic 4T1 mice (n=2) obtained using a 9.4 Tesla MRI before and after administration of the RGD-NC nanoparticles (at a dose of 1.74 mg Fe/kg b.w.). This dose is substantially lower than typical dose of 10 nanoparticles used in MR imaging studies (e.g., 10 mg Fe/kg). MR images were acquired a few minutes prior to injection of the agent and 15, 30, 45 and 60 min after injection. The scanning parameters in the pre- and post-injection images were identical. FIG. 20a compares the pre-injection and 45-min post-injection images of the liver in a metastatic animal. The uptake of the agent by the macrophages in the liver generated an appreciable negative contrast. However, targeting of the RGD-NC nanoparticles to metastatic lesions achieved a significantly higher negative contrast (yellow arrows in FIG. 20a) that 'overshadowed' the background contrast in the liver. As described in the next section, histological evaluation of the liver confirms the accumulation of the agent in metastatic tumors. FIG. 20b shows a 45-min post-injection image of a healthy liver demonstrating that the uptake of the agent in the liver generated homogeneous contrast with no 'hot' spots. To quantitatively evaluate the ability of the RGD-NC nanoparticles to target metastasis, the absolute MR signal intensity in the metastatic lesions and the healthy liver was measured using manually drawn regions of interest (ROI). FIG. 20c shows that the time-course of the signal intensity in the hot spots or the entire healthy liver (normalized to the signal of an adjacent muscle; scale: 0-1). Lower values indicate greater contrast in T2 images, and a normalized intensity value of 1 corresponds to no contrast compared to the pre-contrast image. The pre-injection values for both the normal liver and the 'hot' spots in the metastatic liver were fairly similar and close to 1. As expected, due to clearance of the particles by the liver, injection of RGD-NC resulted in contrast enhancement in the healthy liver with an intensity value of 0.83. However, the metastatic lesions exhibited a normalized signal intensity value of ~0.44 in the post-injection images, indicating significantly higher contrast compared to the post-injection background signal of the healthy or uninvolved regions of the metastatic liver. It is important to note that this contrast may be further improved by optimization of the MRI imaging parameters or by quantifying the T2* relaxation values directly.

Histological Evaluation

After the last in vivo imaging session, tissues were collected and histological analysis was performed to confirm the localization of the RGD-NC nanoparticles in metastatic tumors. We histologically examined the animals used in the in vivo imaging studies verifying the presence of RGD-NC nanoparticles in the majority of metastases. We evaluated the location of the metastatic cancer cells with respect to blood vessels and the associated expression of αvβ3 integrin. Using fluorescence microscopy, we verified that metastatic tumors were present in the liver and lungs of all the animals at a late stage (week 5 after tumor inoculation). Images of entire histological sections of the organs were obtained at a low magnification (5×) using the automated tiling function of the microscope. A representative image of the left lobe of liver is shown in FIG. 21a displaying the presence of clusters of metastatic cells (green) dispersed in the liver parenchyma. Imaging at higher magnification showed that the metastatic cancer cells were localized primarily on the endothelial walls (FIG. 21b). Furthermore, these were exactly the locations that exhibited 'remodeling' as indicated by the overexpression of $α_vβ_3$ integrins (FIG. 21c). We should note that negligible integrin expression was observed in the normal parenchyma of liver (images not shown). The expression of integrins of metastatic cancer cells on the endothelium should favor vascular targeting of the RGD-NC nanoparticles to metastatic tumors. Indeed, fluorescence microscopy showed that RGD-NC particles were predominantly distributed around those same blood vessels colonized by 4T1 cells. Furthermore, the nanoparticles colocalized with the integrin expression of 4T1 cancer cells (FIGS. 21d-f). In addition to fluorescence microscopy showing the colocalization of cancer cells and RGD-NC particles, bright field microscopy was performed on the same histological sections after standard hematoxylin-eosin staining (FIGS. 21g-h).

We also performed histological analysis on the lungs of the same animals. FIG. 20a shows that micrometastases were present in the lungs at week 5 after tumor inoculation. Similarly to the liver, the RGD-NC particles accumulated in those locations that were colonized by metastatic cancer cells (FIG. 22b). Notably, FIGS. 22c-e indicate that the location of RGD-NC coincided with overexpression of $α_vβ_3$ integrins on the metastasized cancer cells.

In this Example, we thus demonstrated that the geometry of a chain-shaped nanoparticle promoted targeting of metastatic tumors due to multivalent docking onto integrins of the vascular bed of metastasis. Using multimodal in vivo imaging (i.e., FMT and MRI), we were able to image metastatic tumors in the liver and lungs in a highly aggressive breast tumor model. As the biological mechanisms of metastasis continue to unravel, we expect that more surface markers of metastatic lesions will be identified that can be employed by nanoparticle delivery systems for targeting metastatic disease.

Example 4

In this example, we show that a dual-ligand nanoparticle provides a unique opportunity to image micrometastases. The nanoparticle is comprised of iron oxide (IO) nanospheres chemically linked into a linear nanochain. The aspect ratio of targeted nanochains substantially increases the probability of associating with metastatic lesions due to geometrically enhanced multivalent docking on the vasculature of metastasis. Furthermore, the nanochains exhibit higher magnetic relaxivity compared to their constituent spheres, which facilitated detection of metastases in a murine breast tumor model using MRI. Furthermore, by selecting two appropriate chemical specificities, a dual-ligand strategy can provide both synergistic amplification of nanoparticle targeting to micrometastases expressing both receptors but also detection of metastatic tumors expressing only one receptor that would be otherwise missed using a single-ligand strategy.

Specifically, we designed a dual-ligand system that utilizes peptides targeting the integrin and EGF receptors. Both αvβ3 integrin and EGFR are functionally linked to the development of breast cancer metastasis. Since cooperation between integrins and EGFR affects many aspects of tumor metastasis, metastases frequently co-express both receptors. More importantly, micrometastasis may overexpress only one of the receptors, emphasizing the need for a dual-ligand approach that can identify a broader range of tumors.

Our results show that dual-ligand integrin- and EGFR-targeting nanochains co-localized in metastases expressing both EGFR and $α_vβ_3$ integrin or only one of these receptors (FIG. 23). A cocktail of three different targeted nanochains was injected to animals bearing 4T1 metastases (n=3). The cocktail contained $α_vβ_3$ integrin-targeting nanochains (single-RGD-NC), EGFR-targeting nanochains (single-EGFR-NC) and dual-ligand nanochains (dual-ligand NC). Imaging was performed using fluorescence molecular tomography (FMT). Different NIR dyes on the three nanochains allowed us to visualize the in vivo fate of all three formulations in the same animal. FIG. 23a shows that the dual-ligand nanochain captured metastases that would be otherwise missed if only one ligand was used. While single-RGD-NC and single-EGFR-NC co-localized in a subset of metastases (FIG. 23b), many metastases were targeted only by single-EGFR-NC or single-RGD-NC. The in vivo imaging data were verified histologically. Even though the sample size in this study was relatively small (n=3), the detectability (on a per lesion basis) of the dual-ligand approach was about 90% in comparison to 37% and 56% for single-EGFR and single-RGD nanochains, respectively. Taking under consideration the microenvironment of micrometastasis, a dual-ligand nanoparticle capable of 'complementary sensing' $α_vβ_3$ integrin and/or EGF receptors on the remodeled vascular bed of metastases offers an enhanced capacity to specifically recognize micrometastasis. Since extravascular metastases are preceded by metastatic cancer cells residing inside the lumen of blood vessels, our data demonstrate that nanochains with EGFR- and $α_vβ_3$-integrin-binding peptides detect micrometastasis (detectability>90%) that would be otherwise missed using a single-ligand strategy (detectability<56%).

Example 5

In this example, we designed a multicomponent nanoparticle capable of 1) transporting a large drug cargo to metastases via targeting the metastasis-associated vasculature and 2) responding to a stimulus resulting in on-command spread of its cargo. The nanoparticle is comprised of three iron oxide (IO) nanospheres and one drug-loaded liposome chemically linked into a linear assembly.

Firstly, the high aspect ratio and flexibility of the nanochains substantially increase their probability of homing to metastases due to geometrically enhanced multivalent docking to the vasculature of metastases. Since vascular targeting does not require the EPR effect as a prerequisite, we showed that $α_vβ_3$ integrin-mediated vascular targeting of nanochains effectively targeted metastasis, which facilitated detection of micrometastases using MRI. The adhesion of cancer cells onto vessel walls is mediated by $α_vβ_3$ integrin receptors on both the cancer cell and the endothelial cell, which are crosslinked by fibrinogen. Secondly, once the nanochains bind at the target site, a mild radiofrequency (RF) field can rapidly release the drug due to defects of the liposomal membrane caused by the oscillation of the IO 'tail' of the nanochain. In a recent animal study, RF-triggered release of a potent chemotherapeutic (doxorubicin or DOX) from the nanochains resulted in a wide-spread cytotoxic effect throughout the tumor volume.

Both integrin-targeting and RF-triggered release of drug exhibits significantly high therapeutic benefits. Animal bearing 4T1 metastases were treated with integrin-targeting DOX-loaded nanochains (termed RGD-DOX-NC). Using in vivo bioluminescence imaging (BLI) of the Luc-4T1 cells, the response of the metastatic tumors was monitored. FIG. 24a shows representative images of RGD-DOX-NC-treated animals with or without application of RF. Notably, FIG. 24b shows the quantitative assessment indicating that vascular targeting of nanochain followed by RF resulted in a significant enhancement of the treatment of metastases that that would be otherwise negligible in the absence of RF application.

From the above description of the application, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

6. The method of claim 1, the liposome, lipidic nanoparticle, or polymer nanoparticle including the anticancer agent.

7. The method of claim 1, the nanochain including at least one targeting moiety linked to a nanoparticle of the nanochain.

8. The method of claim 1, the nanochain including multiple targeting moieties linked to nanoparticles of the nanochain, wherein the spacing and location of the targeting moieties on each nanoparticle is controlled to facilitate delivery, targeting, and/or therapeutic efficacy of the nanochain when administered to a subject.

9. The method of claim 1, the multi-component nanochain including at least two metal nanoparticles and a liposome, lipidic nanoparticle, or polymer nanoparticle linked together to form the nanochain, at least one of the metal nanoparticles having asymmetric surface chemistry defined by asymmetrically disposed first linkers and second linkers, the metal

Having described the invention, the following is claimed:

1. A method of treating cancer in a subject, the method comprising:
   administering to the subject a multi-component nanochain that includes at least three nanoparticles linked together to form the nanochain, at least one nanoparticle of the nanochain having asymmetric surface chemistry defined by asymmetrically disposed first linkers and second linkers, the nanoparticles being linked to form the nanochain by linking first linkers and/or second linkers disposed on separate nanoparticles, at least one nanoparticle comprising or being linked to an anti-cancer agent.

2. The method of claim 1, the nanoparticles having a diameter of about 1 nm to about 50 nm and the nanochain having a length less than about 200 nm and a width about 50 nm or less.

3. The method of claim 1, the nanoparticles comprising at least one of a metal nanoparticle, lipidic nanoparticle, polymer nanoparticle, liposome, or dendrimer.

4. The method of claim 1, the nanoparticles comprising at least one iron oxide nanoparticle or gold nanoparticle.

5. The method of claim 1, the nanoparticles further comprising a liposome, lipidic nanoparticle, or polymer nanoparticle linked to a metal nanoparticle.

nanoparticles and the liposome, lipidic nanoparticle, or polymer nanoparticle being linked to form the nanochain by linking the first linkers and/or second linkers disposed on separate metal nanoparticles and the liposome, lipidic nanoparticle, or polymer nanoparticle, the liposome, lipidic nanoparticle, or polymer nanoparticle including the anti-cancer agent, the metal nanoparticles being responsive to energy, from a remote source that is effective to release the anti-cancer agent from the liposome, lipidic nanoparticle, or polymer nanoparticle after administering the nanochain to a subject.

10. The method of claim 9, the nanochains being delivered intravenously to the subject and applying an energy from the remote energy source to the administered nanochains localized to cancer cells of the cancer to release the anti-cancer agent from the liposome, lipidic nanoparticle, or polymer nanoparticle.

11. The method of claim 10, the remote energy source being external the subject.

12. The method of claim 11, the energy source comprising a radiofrequency (RF) energy source, the metal nano-particles resonating or oscillating upon application of a radiofrequency (RF) energy from the energy source effective to release the anti-cancer agent from the liposome, lipidic nanoparticle, or polymer nanoparticle.

13. The method of claim 12, the RF energy effective to release the anti-cancer agent being an amount less than that required to induce a localized temperature increase in the subject.

14. The method of claim 12, the metal nano-particles being iron oxide nanoparticles, one of the iron oxide nanoparticles being linked to a liposome that includes the anti-cancer agent.

15. The method of claim 10, the energy source comprising a radiation energy source, the metal nano-particles heating upon application of energy from the energy source effective to release the anti-cancer agent from the liposome, lipidic nanoparticle, or polymer nanoparticle.

16. The method of claim 15, the radiation energy comprising electromagnetic radiation that is effective to release the anti-cancer being an amount that induces a localized temperature increase in the subject.

17. The method of claim 1, anti-cancer agent comprising at least one of a chemotherapeutic agent or photosensitizer.

18. The method of claim 10, further comprising imaging the cancer of the subject to determine when the nanochains are localized to the cancer cells of the cancer.

\* \* \* \* \*

SEQUENCE LISTING

```
<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

Tyr His Trp Tyr Gly Tyr Thr Pro Gln Asn Val Ile
1               5                   10

<210> SEQ ID NO 2
<211> LENGTH: 5
<212> TYPE: PRT
<213> ORGANISM: Homo sapiens

<400> SEQUENCE: 2

Arg Gly Asp Phe Cys
1               5
```